(12) United States Patent
Hunsberger et al.

(10) Patent No.: US 12,157,007 B2
(45) Date of Patent: *Dec. 3, 2024

(54) NEUROMODULATION OF GANGLIA

(71) Applicant: Galvani Bioelectronics Limited, Stevenage (GB)

(72) Inventors: Gerald Edwin Hunsberger, Collegeville, PA (US); Arun Sridhar, Stevenage Hertfordshire (GB)

(73) Assignee: Galvani Bioelectronics Limited, Stevenage (GB)

( * ) Notice: Subject to any disclaimer, the term of this patent is extended or adjusted under 35 U.S.C. 154(b) by 32 days.

This patent is subject to a terminal disclaimer.

(21) Appl. No.: 17/893,924

(22) Filed: Aug. 23, 2022

(65) Prior Publication Data
US 2023/0018108 A1 Jan. 19, 2023

Related U.S. Application Data

(63) Continuation of application No. 16/771,441, filed as application No. PCT/GB2018/053599 on Dec. 11, 2018, now Pat. No. 11,464,976.

(60) Provisional application No. 62/597,256, filed on Dec. 11, 2017.

(51) Int. Cl.
*A61N 1/05* (2006.01)
*A61N 1/36* (2006.01)

(52) U.S. Cl.
CPC ......... *A61N 1/3605* (2013.01); *A61N 1/0556* (2013.01); *A61N 1/36114* (2013.01)

(58) Field of Classification Search
CPC . A61N 1/36114; A61N 1/0556; A61N 1/3605
See application file for complete search history.

(56) References Cited

U.S. PATENT DOCUMENTS

| | | | |
|---|---|---|---|
| 8,155,744 B2* | 4/2012 | Rezai | A61F 2/82 607/42 |
| 11,464,976 B2* | 10/2022 | Hunsberger | A61N 1/0556 |
| 2009/0149912 A1 | 6/2009 | Dacey, Jr. et al. | |
| 2012/0277839 A1 | 11/2012 | Kramer et al. | |
| 2017/0095667 A1 | 4/2017 | Yakovlev et al. | |
| 2021/0069511 A1* | 3/2021 | Hunsberger | A61N 1/36114 |

FOREIGN PATENT DOCUMENTS

WO 2004075974 A2 9/2004

OTHER PUBLICATIONS

Tricia M. Mckeever, Philip J. Weston, Richard Hubbard, Andrew Fogarty, Lung Function and Glucose Metabolism: An Analysis of Data from the Third National Health and Nutrition Examination Survey, American Journal of Epidemiology, vol. 161, Issue 6, Mar. 15, 2005, pp. 546-556. (Year: 2005).*

\* cited by examiner

*Primary Examiner* — Alyssa M Alter
(74) *Attorney, Agent, or Firm* — McAndrews, Held & Malloy, Ltd.

(57) ABSTRACT

Modulation of neural activity of a ganglion, by applying a signal to a sympathetic nerve adjacent to the ganglion, results in preferential reduction of sympathetic signals to an effector, thereby providing ways of treating and preventing conditions associated with exacerbated sympatho-excitation.

18 Claims, 7 Drawing Sheets

The first configuration

The second configuration

Unbalanced current density

Key: ● Target ganglion  ◎ Optional target ganglion
← Preferential direction of propagation of action potential Key: ● Target ganglion  ◎ Optional target ganglion
← Preferential direction of propagation of action potential

NEUROMODULATION OF GANGLIA

CROSS-REFERENCE TO RELATED APPLICATIONS

This application is a continuation of U.S. patent application Ser. No. 16/771,441 filed Jun. 10, 2020, which is a U.S. National Stage application under 35 U.S.C. § 371 of International Application PCT/GB2018/053599 (published as WO 2019/116029 A1) filed Dec. 11, 2018, which claims the benefit of priority to U.S. provisional Application No. 62/597,256 filed Dec. 11, 2017. Each of these prior applications are hereby incorporated by reference in their entirety.

TECHNICAL FIELD

This invention relates to neuromodulation of ganglia to achieve therapeutic effects. More specifically, the invention relates to medical devices and systems that modulate the neural activity of ganglia to achieve therapeutic effects.

BACKGROUND ART

A ganglion is made of cell bodies of afferent and efferent nerves. Ganglia often interconnect with other ganglia to form a complex system of ganglia. Ganglia provide relay points and intermediary connections between different neurological structures in the body, such as the peripheral and central nervous systems.

Therapeutic treatments involving targeting the ganglia have been investigated. For example, attempts to treat cardiac dysfunctions such as ventricular arrhythmias include targeting ganglia within the cardiac sympathetic nervous system by electrical stimulation or transection, which resulted in modulation of autonomic imbalances and reduced arrhythmias. One surgical approach to treat ventricular arrhythmias involves the resection of stellate ganglion [1,2,3,4]. Electrical stimulation of cardiac-related nerves with the aim to treat cardiac disorders has been reported, e.g. in references [5] and [6]. High sympathetic or neural tone can be causative or result in many pathologies, and treatment paradigm might involve reducing the high tone in the ganglia and post ganglionic nerves thereof. Techniques to accomplish this involve conduction block of nerves.

However, treatments that are currently under research typically require a high charge density per phase to produce a therapeutic effect. This is not ideal for clinical applications because of the collateral damage that may be caused by the high charge density per phase applied to the nerve, especially when applied in the long term. Moreover, the high energy requirement because of the high charge density per phase limits battery life of an implant for electrical stimulation. Also, the need to apply a high charge density per phase limits the design options for the neural interfacing elements.

The invention therefore aims to provide further and improved ways of modulating ganglia to achieve therapeutic effects. In particular, the invention aims to provide further and improved ways of treating and preventing conditions where the pathology is driven by exacerbated sympatho-excitation, e.g. cardiac dysfunction, and metabolic disorders which involve impaired glucose control, such as T2D.

SUMMARY OF THE INVENTION

The invention relates to restoring the body's homeostasis by modulating afferent-mediated decreases in central sympathetic drive. This can be achieved by modulating the neural activity of a ganglion which leads to preferential reduction of efferent sympathetic signals to its effector. In particular, the invention involves applying electrical signals having a charge density per phase below a predetermined threshold to a sympathetic nerve at a site adjacent to a ganglion to incite action potentials that preferentially propagate away from an effector, towards the ganglion. This preferentially leads to a change in the electrical properties of the ganglionic cell bodies adjacent to the signal application site, e.g. the ganglion which the action potentials (as created by the signal) travel towards, resulting in reduced efferent sympathetic signals to the effector. The change in electrical properties of the ganglionic cell bodies may involve re-organization to silence the excitatory cell bodies and bring about homeostasis in the ganglionic cell bodies. One of the processes this might result in would be increasing the refractoriness of the ganglionic cell bodies that would make them resistant to incoming volleys from CNS.

Thus, the invention provides a system for reversibly modulating the neural activity of a sympathetic nerve. The system comprises at least two neural interfacing elements suitable for placement on or around the nerve adjacent to a ganglion, wherein the ganglion transmits sympathetic signals between the ganglion and an effector, and at least one voltage or current source configured to generate at least one electrical signal to be applied to the nerve, via the at least two neural interfacing elements, to modulate the neural activity of the nerve to reduce sympatho-excitation in the effector. The at least two neural interfacing elements are configured such that the electrical signal incites action potentials in the nerve that propagate away from the effector, towards the ganglion, and the charge density per phase applied to the nerve by the electrical signal is below a predetermined threshold, the predetermined threshold defined as the minimum charge density per phase required to produce a response associated with sympatho-excitation in the effector by modulating the neural activity of the sympathetic nerve.

The application of an electrical signal having a charge density per phase below the predetermined threshold to a sympathetic nerve at a site adjacent to a ganglion, to incite action potentials that preferentially propagate away from the effector, towards the ganglion (i.e. in the afferent direction) is advantageous because the signal is sufficient to modulate the electrical properties of the nerve causing a change in electrical properties of the ganglionic cell bodies adjacent to the signal application site, such as ganglionic refractoriness, but not sufficient to produce responses that are associated with sympatho-excitation in the effector. Furthermore, the body's regulatory control mechanisms are tightly regulated, and so if the control systems are pushed in one way by exogenous inputs, e.g. by applying an electrical signal having a high charge density per phase (above the predetermined threshold) as disclosed in the prior art, the endogenous reflexes would push back to maintain homeostasis, which would result in reduced efficacy of processing in the ganglia.

The invention is based on literature suggesting that altered neural signaling in nerve structures that contain ganglia, e.g. the sympathetic chain or the GSN, may be associated with an imbalance of sympatho-vagal signaling. For example, cardiac pathology is suggested to be associated with altered neural signaling in cardiac ganglia resulting in an imbalance of sympatho-vagal signaling. This leads to deviations in properties of intracardiac ganglia. Use of neuromodulatory approaches at the sympathetic chain has been shown to result in improvements in cardiac function [7]. It has been reported that unilateral stimulation of the stellate ganglion and the ansae subclavia, respectively, were able to influence the electrophysiological properties of the heart [8,9].

The invention is also supported by a report showing that refractoriness in a nerve in mice can be caused by low frequency stimulation (1 Hz) [10]. It was found that the refractoriness may be caused by intensified internalization of sodium channels leading to irreversible decline of the compound action potential amplitude.

It has also been demonstrated in other nerve structures that low frequency stimulation of these nerve structures led to depression in postganglionic transmission, contributing to the reduction in sympathetic tone. These nerve structures are similar in that they contain ganglia, convey both afferent and efferent sympathetic signals, and the signal transmissions are complex involving extensive ganglionic processing. For example, the inventors found that directional stimulation of a nerve structure similar to the sympathetic chain ganglia led to refractoriness in neural signaling and impacted on baseline physiology [11]. It was also found that low frequency stimulation of the hypogastric nerves in cats inhibited discharge from the pelvic ganglia, thereby contributing to sympathetic depression of bladder activity [12].

Reference [13] shows that bipolar cervical vagus nerve stimulation reflected a dynamic interaction between afferent mediated decreases in central parasympathetic drive and suppressive effects evoked by directional stimulation of parasympathetic efferent axons to the heart. In particular, Reference [13] shows that different cardiac responses were evoked by changing bipolar electrode orientation (i.e. either anode cephalad to cathode ("cardiac" configuration) which incites action potentials which propagate preferentially towards the heart; or cathode cephalad to anode ("epilepsy" configuration) which incites action potentials towards the brain.

The invention also provides a method for reversibly modulating the neural activity of a sympathetic nerve, comprising: placing at least two neural interfacing elements on or around the nerve adjacent to a ganglion, wherein the ganglion transmits sympathetic signals between the ganglion and an effector; and applying, by at least one voltage or current source, at least one electrical signal to the nerve, via the at least two neural interfacing elements, to modulate the neural activity of the nerve to reduce sympatho-excitation in the effector, wherein the at least two neural interfacing elements are configured such that the electrical signal incites action potentials in the nerve which propagate away from the effector, towards the ganglion, wherein the charge density per phase applied to the nerve by the electrical signal is below a predetermined threshold, the predetermined threshold defined as the minimum charge density per phase required to produce a response associated with sympatho-excitation in the effector by modulating the neural activity of the sympathetic nerve.

The invention also provides charged particles for use in a method of treating or preventing a condition where the pathology is driven by exacerbated sympatho-excitation, wherein the charged particles cause reversible depolarization and hyperpolarization of the nerve membrane of a sympathetic nerve adjacent to a ganglion, such that action potentials that propagate along the nerve toward the ganglion are created de novo in the modified nerve, wherein the ganglion transmits sympathetic signals between the ganglion and an effector, wherein the neural activity of the modified nerve between the ganglion and the effector is modulated to reduce sympatho-excitation in the effector, wherein the charge density per phase of the charged particles is below a predetermined threshold, the predetermined threshold defined as the minimum charge density per phase required to produce a response associated with sympatho-excitation in the effector by modulating the neural activity of a nerve.

The invention also provides a modified sympathetic nerve wherein at least two neural interfacing elements of a system of the invention are attached to the nerve adjacent to a ganglion, wherein the at least two neural interfacing elements are in signaling contact with the modified nerve and so the modified nerve can be distinguished from the nerve in its natural state, and wherein the nerve is located in a patient who suffers from a condition where the pathology is driven by exacerbated sympatho-excitation.

The invention also provides a modified sympathetic nerve having a nerve membrane that is reversibly depolarized and hyperpolarized by charged particles, the depolarization and hyperpolarization being induced by applying an electrical signal at the nerve adjacent to a ganglion, wherein the ganglion transmits sympathetic signals between the ganglion and an effector, such that action potentials that propagate along the nerve toward the ganglion are created de novo in the modified nerve, wherein the neural activity of the modified nerve between the ganglion and the effector is modulated to reduce sympatho-excitation in the effector, wherein the charge density per phase of the charged particles is below a predetermined threshold, predetermined threshold defined as the minimum charge density per phase required to produce a response associated with sympatho-excitation in the effector.

The invention also provides a modified sympathetic nerve obtainable by reversibly modulating neural activity of the modified nerve according to a method of the invention.

The invention also provides a modified ganglion adjacent a modified sympathetic nerve of the invention, wherein the modified ganglion has a reduced capacity to transmit sympathetic signals to the effector.

The invention also provides a method of reversibly modulating neural activity in a sympathetic nerve, comprising: (i) implanting in the subject a system of the invention; (ii) positioning the at least two neural interfacing elements of the system at the nerve adjacent to a ganglion; and optionally (iii) activating the system.

The invention also provides a method of controlling the system of the invention, wherein the system is in signaling contact with a sympathetic nerve adjacent to a ganglion, wherein the ganglion transmits sympathetic signals between the ganglion and an effector, the method comprising a step of sending control instructions to the system, in response to which the system applies a signal to the nerve at between the ganglion and the effector, wherein the charge density per phase of the charged particles is below a predetermined threshold, predetermined threshold defined as the minimum charge density per phase required to produce a response associated with sympatho-excitation in the effector.

The invention also provides a computer-implemented method comprising reversibly modulating the neural activity of a sympathetic nerve, the method comprises: applying by at least one voltage or current source of a system of the invention, at least one electrical signal to the nerve adjacent to a ganglion, via at least two neural interfacing elements, to modulate the neural activity of the nerve to reduce sympatho-excitation in the effector, wherein the at least two neural interfacing elements are configured such that the electrical signal incites action potentials in the nerve which propagate away from the effector towards the ganglion, wherein the charge density per phase applied to the nerve by the electrical signal is below a predetermined threshold, the predetermined threshold defined as the minimum charge density per phase required to produce a response associated with sympatho-excitation in the effector.

The invention also provides a computer comprising a processor and a non-transitory computer readable storage medium carrying an executable computer program comprising code portions which when loaded and run on the processor cause the processor to: apply, by at least one voltage or current source of a system of the invention, at least one electrical signal to the nerve adjacent to a ganglion, via at least two neural interfacing elements, to modulate the neural activity of the nerve to reduce sympatho-excitation from the ganglion in the effector, wherein the at least two neural interfacing elements are configured such that the electrical signal incite action potentials in the nerve which propagate away from the effector towards the ganglion, wherein the charge density per phase applied to the nerve by the electrical signal is below a predetermined threshold, the predetermined threshold defined as the minimum charge density per phase required to produce a response associated with sympatho-excitation in the effector.

BRIEF DESCRIPTION OF THE DRAWINGS

FIG. 5A shows a first electrode configuration. FIG. 5B shows a second electrode configuration.

FIG. 6A shows an imbalanced surface area configuration. FIG. 6B shows a recessed electrode configuration. FIG. 6C shows an imbalanced insulation configuration.

FIG. 7A shows a single neural interface on the branch between T1-T2 ganglia. FIG. 7B shows a first neural interface on the branch between T1-T2 ganglia, and a second neural interface on the branch between T2-T3 ganglia. C8 represents C8 ganglion, T1 represents T1 ganglion, T2 represents T2 ganglion, T3 represents T3 ganglion, T4 represents T4 ganglion.

FIG. 8A shows a single neural interface at the GSN branch between the suprarenal and celiac ganglia. FIG. 8B shows a first neural interface at the GSN branch between the suprarenal and celiac ganglia, and a second neural interface at the GSN branch between the celiac ganglion and the foregut.

DETAILED DESCRIPTION OF THE INVENTION

Signal Application Site

Figure 1:
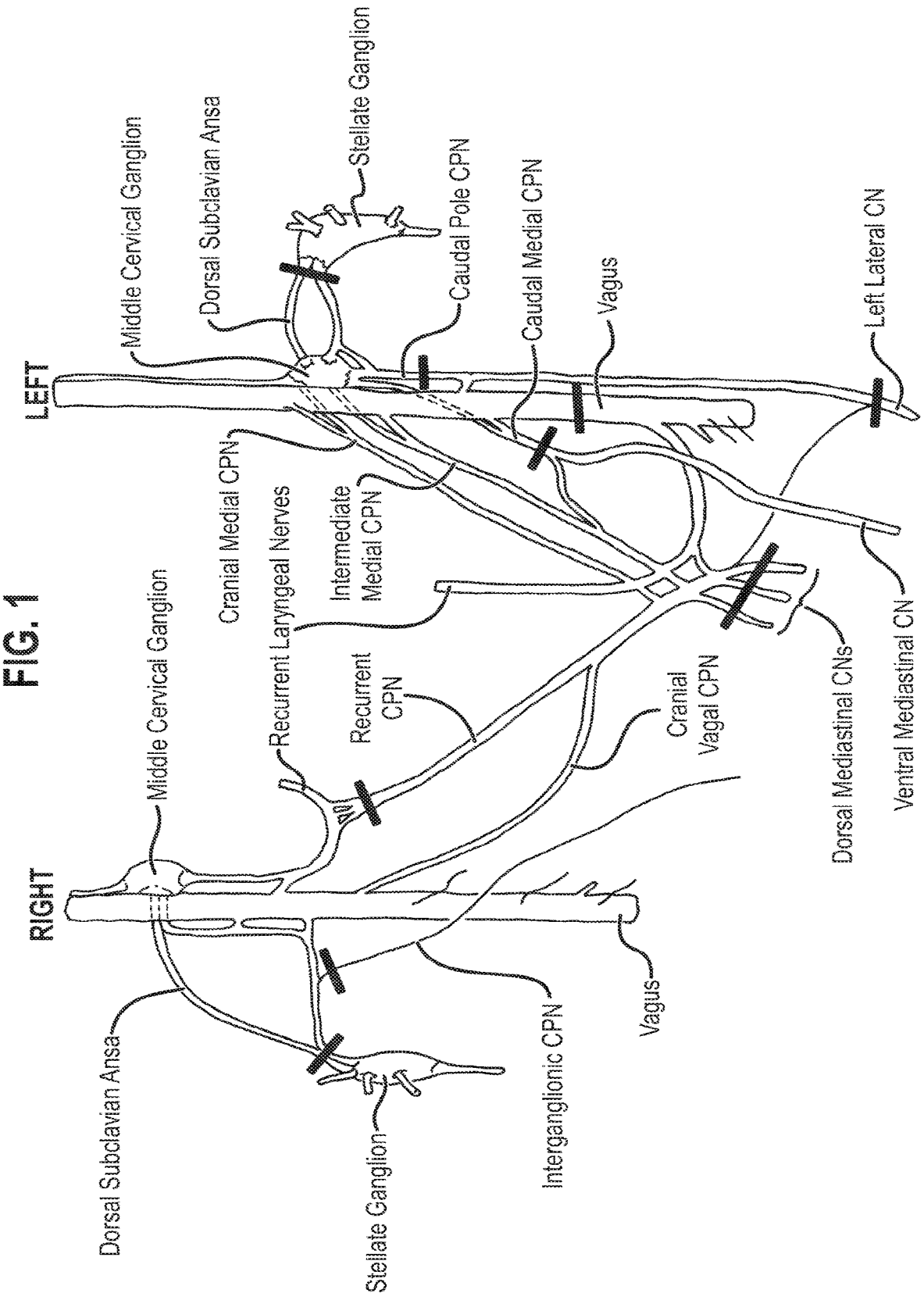
FIG. 1 is a schematic diagram depicting the gross anatomic arrangement of the intrathoracic ganglia and associated mediastinal neural structures.

The invention involves application of an electrical signal to a sympathetic nerve adjacent to a ganglion. For example, the signal application site may be at a sympathetic nerve in the sympathetic chain or in a branch of the greater splanchnic nerve (GSN). In some embodiments, the signal application site may be at an interganglionic nerve branch, e.g. between intrathoracic ganglia in the sympathetic chain, or between the suprarenal and the celiac ganglia. In some embodiments, the signal application site may be between a ganglion and an effector, e.g. between the celiac ganglion and the foregut.

The signal application site is preferentially within 1 cm, 0.5 cm, 0.25 cm, 1 mm, 500 µm, 25 µm, or 10 µm of a ganglion. Without wishing to be bound by theory, it is postulated that the effectiveness in changing the electrical properties of the ganglionic cell bodies (such as ganglionic refractoriness) is proportional to the distance between the signal application site and the ganglionic cell bodies.

The invention involves applying the electrical signal to both afferent and efferent fibers of a sympathetic nerve. For example, the signal incites action potentials, such that orthodromic action potentials travel in the afferent fibers and/or antidromic action potentials travel in the efferent fibers.

Signal application sites that are useful with the invention are discussed further below.

A Cardiac-Related Sympathetic Nerve

The invention aims to restore the heart's homeostasis by modulating afferent-mediated decreases in central sympathetic drive. To cause afferent-mediated decreases in central sympathetic drive, the invention involves inciting action potentials at a certain site in a cardiac-related sympathetic nerve, and this causes changes in the electrical properties of the ganglionic cell bodies adjacent to the signal application site (such as ganglionic refractoriness), thereby resulting in reduced efferent sympathetic signals to the heart.

The signal application site may be at a cardiac-related nerve in an interganglionic branch in the sympathetic chain. Preferably, the interganglionic branch is between intrathoracic ganglia. Intrathoracic ganglia are located within the thorax along the sympathetic chain, and they are arranged in vertebrate animals, such as humans, as follows (in descending order from the rostral end of the spinal cord): the middle cervical ganglion, the inferior cervical ganglion (also known as the C8 ganglion), the T1 ganglion, the T2 ganglion, the T3 ganglion, and the T4 ganglion.

The inferior cervical ganglion is fused with the T1 ganglion to form a single structure called the stellate ganglion in around 80% of the human population. Hence, in certain human individuals, the intrathoracic ganglia are located along the sympathetic chain as follows (in descending order from the rostral end of the spinal cord): the middle cervical ganglion, the stellate ganglion, the T2 ganglion, the T3 ganglion, and the T4 ganglion.

A signal application site that is useful with the invention may be caudal to the middle cervical ganglion, caudal to the inferior cervical ganglion, caudal to the stellate ganglion, caudal to the T1 ganglion, caudal to the T2 ganglion or caudal to the T3 ganglion.

The signal application site may be cranial to the T4 ganglion, cranial to the T3 ganglion, cranial to the T2 ganglion, cranial to the T1 ganglion, cranial to the stellate ganglion, cranial to the inferior cervical ganglion, or cranial to the middle cervical ganglion.

The signal application site may be at one or more interganglionic branches selected from the group consisting of: between the middle cervical and T4 ganglia, between the middle cervical and T3 ganglia, between the middle cervical and T2 ganglia, and between the middle cervical and T1 ganglia, between the middle cervical and stellate ganglia, between the middle cervical and inferior ganglia, between the inferior cervical and T4 ganglia, between the inferior cervical and T3 ganglia, between the inferior cervical and T2 ganglia, between the inferior cervical and T1 ganglia, between the stellate and T4 ganglia, between the stellate and T3 ganglia, between the stellate and T2 ganglia, between T1 and T4 ganglia, between T1 and T3 ganglia, between T1 and T2 ganglia, between T2 and T4 ganglia, between T2 and T3 ganglia, and between T3 and T4 ganglia. The signal application site may be at any of these interganglionic branches in the left and/or right sympathetic chain. There may be one or more application sites on each interganglionic branch.

The application site may be at the ansae subclavia. The ansae subclavia in an interganglionic nerve branch that possesses nerve cords that surround the subclavian artery, and form the primary interconnection between the stellate, middle cervical and the mediastinal ganglia (see FIG. 1) [14,15]. The dorsal ansae subclavia arise as a craniomedial extension of the stellate ganglion and are usually shorter and thicker than the ventral ansae, which loop anteriorly around the subclavian artery. There is anatomical heterogeneity in that each individual may have one or more ansae subclavia. For example, the ansae subclavia can exist as single or multiple nerve cords, and the right side tends to have more nerve cords in total than the left. There are variations according to the origin and termination of the loop, for example, in some individuals no distinct dorsal ansae can be seen because the stellate and the inferior-most middle cervical ganglia form a large swelling. Thus, the signal application site may be at one or more of the ansae subclavia.

In embodiments where the signal is applied below a predetermined threshold at the ansae subclavia, and the signal incites action potentials in the direction away from the heart, i.e. in the direction from the middle cervical ganglion to the stellate ganglion or the T1 ganglion (depending on the individual, as mentioned above the inferior cervical ganglion may have fused with the T1 ganglion in certain individuals). This may result in refractoriness in the ganglia in the sympathetic chain, e.g. preferentially in the stellate/T1 ganglion, or in both the middle cervical ganglion and the stellate/T1 ganglion, leading to the reduction of sympathetic neural signals from the ganglia to the heart.

The signal application site is preferably at or caudal to the ansae subclavia along the sympathetic chain. This is because the ansae subclavia represents the lowest nexus point in the cardiac nervous system hierarchy for sympathetic projection to the heart that is amenable to the neural interfacing element. From the ansae subclavia, the cardiac-related sympathetic nerves become more diffused so it is practically more difficult to target them. The site of signal application may be at the junction between the dorsal and ventral rami of the ansae subclavia adjacent to the stellate ganglion.

Preferably, the signal application site is cranial to the T3 ganglion along the sympathetic chain, which includes the ansae subclavia. Minimal exogenous neural modulation disturbances to the T3 element and the more caudal elements of the sympathetic chain is advantageous because they are associated with sensory and sympathetic motor control of upper limb, neck and thoracic wall, so the risks for upper limb and thoracic wall pain syndromes and anhydrosis can be minimized. The invention therefore preferably applies the signal to a cardiac-related sympathetic nerve at an interganglionic branch in the sympathetic chain that is cranial to the T3 ganglion.

The signal application site is preferably between the T2 ganglion and the ganglion cranial to T2, which may be the stellate ganglion or the T1 ganglion. The specific anatomical structure that is modulated would depend on the anatomical arrangement of the individual. This region is amenable for neural interfacing element (e.g. electrode) attachment. Also, modulation of neural activity in this region minimizes adverse or off-target effects, as explained above.

Thus, preferably, the signal application site is between the T1 and T2 ganglia. According to the invention, when the invention involves applying a signal below a predetermined threshold at the sympathetic chain between the T1-T2 ganglia, and the signal incites action potentials which propagate preferentially in the direction away from the heart, i.e. from the T1 ganglion to the T2 ganglion, this may result in refractoriness in the ganglia in the sympathetic chain, e.g. preferentially in the T2 ganglion, or in both the T1 and T2 ganglia, leading to the reduction of sympathetic neural signals from the ganglia to the heart.

Preferably, the signal application site is between the inferior cervical and T1 ganglia. According to the invention, when the signal is applied below a predetermined threshold at the ansae subclavia, and the signal incites action potentials in the direction away from the heart, i.e. in the direction from the inferior cervical ganglion to the T1 ganglion, this may result in refractoriness in the ganglia in the sympathetic chain, e.g. preferentially in the inferior cervical ganglion, or in both the inferior cervical and T1 ganglia, leading to the reduction of sympathetic neural signals from the ganglia to the heart.

The signal application site may be between the T2 and T3 ganglia. According to the invention, when the signal is applied below a predetermined threshold at the sympathetic chain between the T2-T3 ganglia, and the signal incites action potentials which propagate preferentially in the direction away from the heart, i.e. in the direction from the T2 ganglion to the T3 ganglion, this may result in refractoriness in the ganglia in the sympathetic chain, e.g. preferentially in the T3 ganglion, or in both the T2 and T3 ganglia, leading to the reduction of sympathetic neural signals from the ganglia to the heart.

Ideally, the signal application site at the interganglionic branch is amenable to neural interfacing element. For example, the nerve is accessible for the neural interfacing element, and is not obstructed by ganglia, branching nerves, other nerves or blood vessels. For example, the interganglionic branch between the T1 and T2 is amenable to neural interfacing element (e.g. electrode) attachment. As well as being accessible, the T1-T4 region tends to be consistent from patient to patient, thus facilitating this site for general use. The T1-T4 and T1-T2 regions have been previously used as a point of intervention [16].

Plasticity exists for cardiac-related sympathetic nerves in the extracardiac intrathoracic neural circuits. For example, neural remodeling including neuron cell body hypertrophy, increased fibrosis, and increased synaptic density have been shown to occur in the left and in both stellate ganglia in patients with cardiomyopathy and in an animal model of myocardial infarction [17,18]. Thus, the exact site for signal application may vary from human to human, but is nonetheless at an interganglionic branch between the intrathoracic ganglia in the sympathetic chain.

The sympathetic chain lies on either side of the vertebral column and essentially extends along its length. Thus, when the invention refers to a cardiac-related nerve in an interganglionic branch between the intrathoracic ganglia in the sympathetic chain, it may be referring to the interganglionic branches in the right and/or left sympathetic chain. Hence, the electrical signal may be applied unilaterally or bilaterally at cardiac-related nerves in interganglionic branches between the intrathoracic ganglia in the sympathetic chain. Modulation of neural activity of one instead of both sides may be sufficient for achieving beneficial physiological effects. This is advantageous because it minimizes the interruption of neural activity, thereby minimizes any adverse off-target effects. When applying the signal bilaterally at cardiac-related nerves in interganglionic branches between the intrathoracic ganglia in the sympathetic chain, the signal may be applied sequentially or simultaneously.

For example, the signal application site may be at the right and/or the left ansae subclavia.

The signal application site may be between the T1 and T2 ganglia in the right and/or the left sympathetic chain.

The signal application site may be between the T2 and T3 ganglia in the right and/or the left sympathetic chain.

Figure 3:
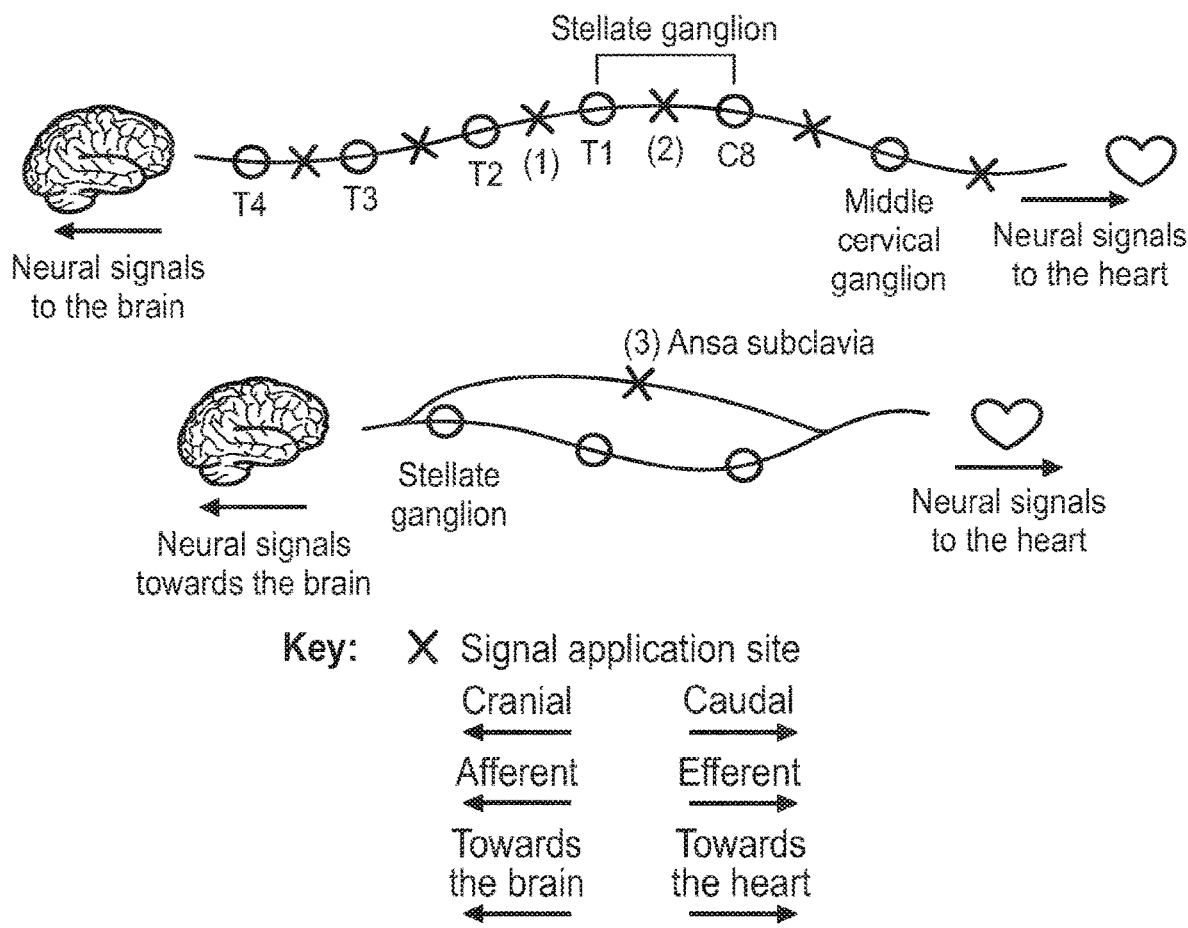
FIG. 3 is a schematic diagram depicting neural interface arrangements on the sympathetic chain.

The application sites of the cardiac-related nerve discussed above are summarized in FIG. 3.

Where the invention refers to a modified cardiac-related nerve, this nerve is ideally present in situ in a subject.

Greater Splanchnic Nerve (GSN)

The invention aims to restore the foregut's homeostasis (e.g. glucose metabolism) by modulating afferent-mediated decreases in central sympathetic drive. To cause afferent-mediated decreases in central sympathetic drive, the invention involves inciting action potentials at a certain site in a branch of the greater splanchnic nerve (GSN), and this causes changes in the electrical properties of the ganglionic cell bodies adjacent to the signal application site (such as ganglionic refractoriness), thereby resulting in reduced efferent sympathetic signals to the foregut.

Figure 2:
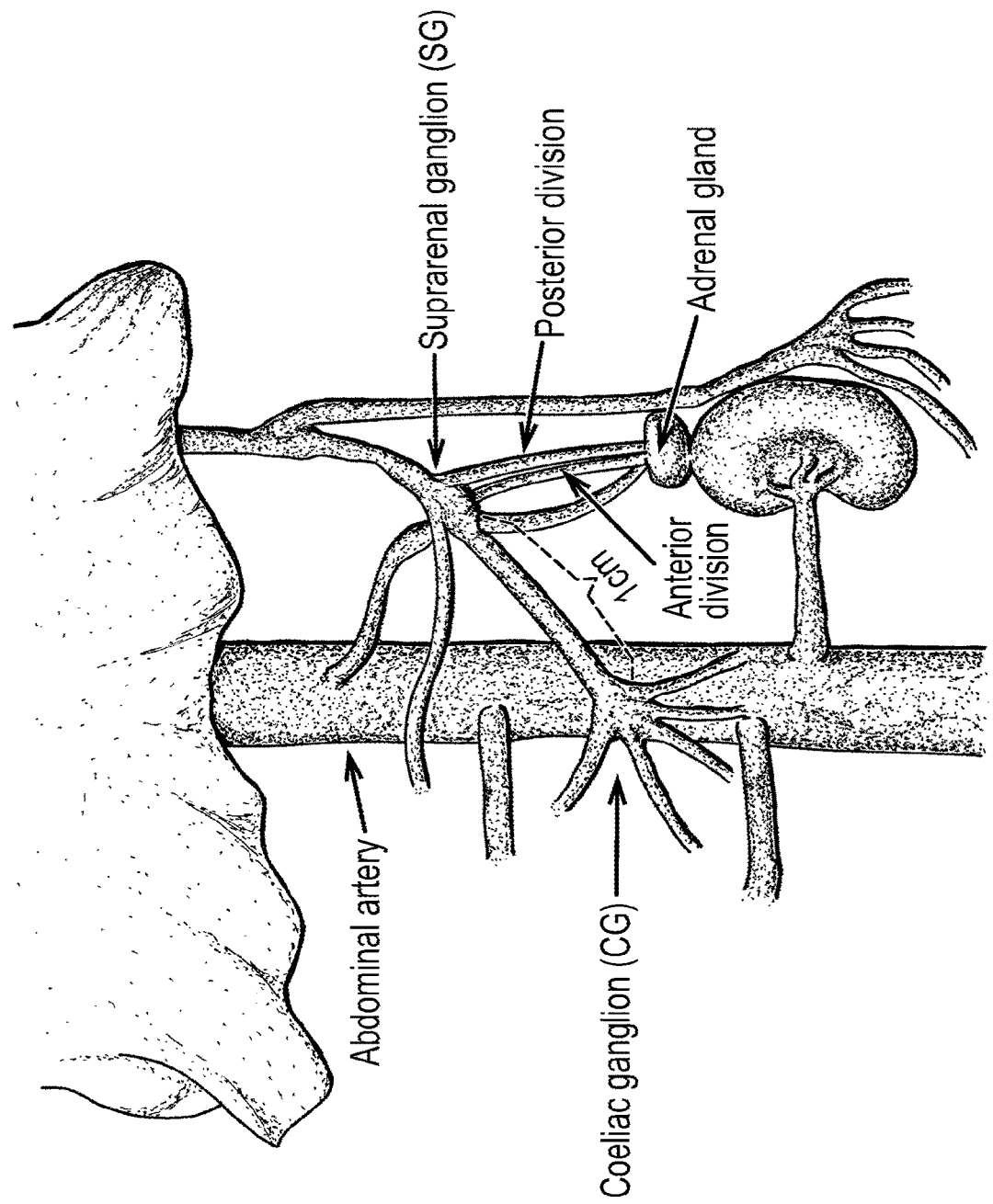
FIG. 2 is a schematic diagram depicting the gross anatomic arrangement of the adrenal innervation. The adrenal glands, abdominal artery, celiac ganglion, suprarenal ganglion, and the posterior and anterior divisions of the branch of the GSN supplying the adrenal gland between the suprarenal ganglion and the adrenal gland are labelled.

The splanchnic nerves carry fibers of the autonomic nervous system (visceral efferent fibers) and sensory fibers from various organs (visceral afferent fibers). All splanchnic nerves carry sympathetic fibers, except for the pelvic splanchnic nerves. The thoracic splanchnic nerves are recognized as medial branches from the lower seven thoracic sympathetic ganglia. They are pre-synaptic nerves of the sympathetic system, and include the GSN, the lesser splanchnic nerve, and the least splanchnic nerve. They pass through the diaphragm to send fibers to the celiac, aorticorenal, and superior mesenteric ganglia and plexuses (see Reference [19]). The GSN synapses at the suprarenal ganglion, and then travels to the celiac ganglion where it synapses, and then travel to and innervates the enteric nervous system of the foregut (see FIG. 2).

The GSN naturally projects sympathetic signals to the enteric nervous system of the foregut, stimulating glucose metabolism for example. Altering neural signaling in the GSN, e.g. the celiac plexus, has also been shown to modulate sympatho-excitation, e.g. resulting in modulation of glucose control or mesenteric vascular resistance. For example, there is evidence in the literature for hepatic sympathetic signaling to be contributory to type 2 diabetes, e.g. renal denervation technology by Metavention which focusses on hepatic sympathetic denervation for improving glucose control. Reference [20] shows that signals from the duodenum via TRPV1 sensitive fibers are key to impaired glucose handling and ablation of TRPV1 fibers using RTX improves OGTT profiles in Sprague-dawley rats. The inventors have also observed that GSN denervation is capable of improving glucose control [21]. There is also evidence in the literature to suggest that blocking sympathetic signals in the celiac plexus leads to lowering of mesenteric vascular resistance and as a result lowering of systemic blood pressure [22,23].

Figure 4:
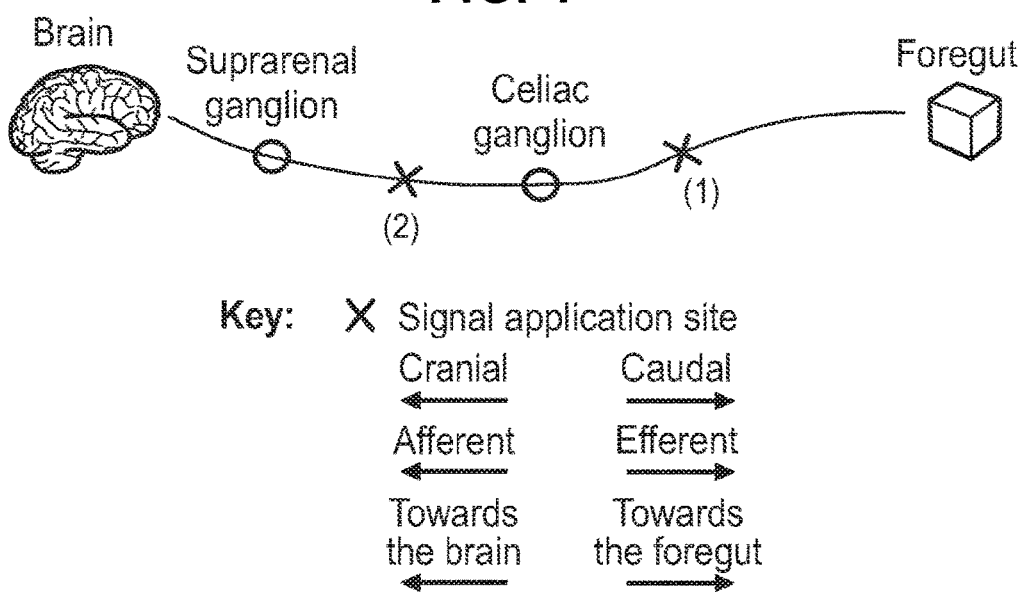
FIG. 4 is a schematic diagram depicting neural interface arrangements on the greater splanchnic nerve.

Examples of signal application sites at the GSN that are useful with the invention are shown in FIG. 4 (e.g. (1) and (2)). These sites are amenable to surgical intervention and neural interfacing element attachment.

In some embodiments of the invention, the signal application site may be at a branch of the GSN between the suprarenal and celiac ganglia (e.g. signal application site (2) in FIG. 4). When the electrical signal incites action potentials that propagate preferentially in the direction away from the foregut, i.e. in the direction from the celiac ganglion to the suprarenal ganglion, this may result in refractoriness in the ganglia, e.g. preferentially in the suprarenal ganglion, or in both the celiac and the suprarenal ganglia, leading to the reduction of sympathetic neural signals to the enteric nervous system of the foregut. This may lead to increasing glucose tolerance, thereby assisting in treating conditions associated with impaired glucose control. This may also lead to lowering of mesenteric vascular resistance that would be beneficial for treating hypertension, heart failure with reduced ejection fraction or heart failure with preserved ejection fraction.

In some embodiments of the invention, the signal application site may be at a branch of the GSN between the celiac ganglion and the foregut (e.g. signal application site (1) in FIG. 4). When the electrical signal incites action potentials that propagate preferentially in the direction away from the foregut, i.e. in the direction from the foregut to the celiac ganglion, this may result in refractoriness in the celiac ganglion, leading to the reduction of sympathetic neural signals from the celiac ganglion to the enteric nervous system of the foregut. This may lead to increasing glucose tolerance, thereby assisting in treating conditions associated with impaired glucose control. This may also lead to lowering of mesenteric vascular resistance that would be beneficial for treating hypertension, heart failure with reduced ejection fraction or heart failure with preserved ejection fraction.

There are two GSNs in the human body and, while signal application to either (i.e. unilateral signal application) or both (i.e. bilateral signal application) is possible according to the invention, the GSN of particular interest is the left GSN. The left GSN is more surgically accessible.

Where the invention refers to a modified greater splanchnic nerve, this nerve is ideally present in situ in a subject.

Modulation of Neural Activity

As explained above, the invention involves modulating afferent-mediated decreases in central sympathetic drive, and this is achieved by modulating the neural activity of a ganglion which leads to preferential reduction of efferent sympathetic signals to its effector. Modulation of neural activity, as used herein, is taken to mean that the signaling activity of the nerve is altered from the baseline neural activity—that is, the signaling activity of the nerve in the subject prior to any intervention. As used herein, "neural activity" of a nerve means the signaling activity of the nerve, for example the amplitude, frequency and/or pattern of action potentials in the nerve. The term "pattern", as used herein in the context of action potentials in the nerve, is intended to include one or more of: local field potential(s), compound action potential(s), aggregate action potential(s), and also magnitudes, frequencies, areas under the curve and other patterns of action potentials in the nerve or sub-groups (e.g. fascicules) of neurons therein. The invention involves modulating the neural activity of at least part of a nerve according to the invention. Modulation of neural activity may also be across the whole nerve.

The invention involves applying electrical signals to incite action potentials in the direction towards a particular ganglion that transmits sympathetic signals to an effector (i.e. to cause directional stimulation of neural activity). Stimulation of neural activity, as used herein, is taken to mean that the signaling activity of the nerve is increased from the baseline neural activity. Directional stimulation, as used herein, is taken to mean an increase in signaling activity of the nerve from baseline neural activity preferentially in one direction along the nerve axis.

As described herein, the invention involves modifying the neural activity of the sympathetic nerve and the ganglion. A way to create a modified sympathetic nerve and ganglion can involve three aspects. The first aspect is to stimulate the neural activity of the nerve, resulting in the creation of action potentials which propagate in both directions along the nerve axis. The second aspect is to arrest or slow the action potentials in one direction. Then, the third aspect is when the action potentials propagating in the other direction are allowed to reach the adjacent ganglion. The action potentials modulate the neural activity of that ganglion such that it operates in a modified state, i.e. having a reduced capacity to transmit sympathetic signals to the effector. Thus, the sympathetic nerve, to which the signal has been applied according to the invention, is operating in a modified state.

These aspects are described in further detail below.

In the first aspect, a first electrical signal, in the form of a temporary external electrical field, when applied at a particular point in the nerve (via a first electrode; anode), artificially modifies the distribution of potassium and sodium ions within that point in the nerve, causing depolarization of the nerve membrane that would not otherwise occur. The depolarization of the nerve membrane caused by the temporary external electrical field gives rise to de novo action potentials which propagate in opposite directions along the nerve axis away from the point of the temporary external electrical field.

In the second aspect, a second electrical signal, also in the form of a temporary external electrical field, when applied at a second point adjacent the first point in the nerve (via a second electrode; cathode), artificially modifies the distribution of potassium and sodium ions within that point in the nerve, causing hyperpolarization of the nerve membrane that would not otherwise occur. The hyperpolarization of the nerve membrane caused by the temporary external electrical field arrests or slows the propagation of the de novo action potentials from passing along the nerve axis beyond the point of the temporary external electrical field.

Then, in the third aspect, the de novo action potentials which propagate towards the ganglion change the electrical properties of the ganglionic cell bodies. This may involve re-organization to silence the excitatory cell bodies and bring about homeostasis in the ganglionic cell bodies. One of the processes this might result in would be increasing the refractoriness of the ganglionic cell bodies that would make them resistant to incoming volleys from CNS. Hence, this is a ganglion operating in a modified state. In this modified state, the ganglion has a reduced capacity to transmit sympathetic signals to the effector. Hence, the sympathetic signals that would normally have been transmitted from the CNS to the effector via that ganglion would be reduced.

Where the invention refers to a modified sympathetic nerve and a modified ganglion, this nerve and ganglion are ideally present in situ in a subject.

As it would be understood in the art, the creation generation of action potentials is based on the influence of electrical currents (e.g. charged particles, which may be one or more electrons in an electrode attached to the nerve, or one or more ions outside the nerve or within the nerve, for instance) on the distribution of ions across the nerve membrane. According to the invention, the electrical currents are configured to apply a charge density per phase below a predetermined threshold.

One advantage of the invention is that modulation of the neural activity is reversible. For example, refractoriness in the ganglia of the sympathetic chain is reversible. Hence, the modulation of neural activity is not permanent. That is, upon cessation of the signal, neural activity in the nerve returns substantially towards baseline neural activity within 1-60 seconds, or within 1-60 minutes, or within 1-24 hours (e.g. within 1-12 hours, 1-6 hours, 1-4 hours, 1-2 hours), or within 1-7 days (e.g. 1-4 days, 1-2 days). In some instances of reversible modulation, the neural activity returns substantially fully to baseline neural activity. That is, the neural activity following cessation of the signal is substantially the same as the neural activity prior to the modulation (i.e. prior to the signal being applied). Hence, the nerve or the portion of the nerve has regained its capacity to propagate action potentials.

In other embodiments, modulation of the neural activity may be substantially persistent. As used herein, "persistent" is taken to mean that the modulated neural activity has a prolonged effect. That is, upon cessation of the signal, neural activity in the nerve remains substantially the same as when signal was being applied—i.e. the neural activity during and following a signal being applied is substantially the same. However, reversible modulation is preferred.

Charge Density Per Phase Below a Predetermined Threshold

The charge density per phase ($C/cm^2$/phase) applied to nerve according to the invention by the electrical signal is below a predetermined threshold. In particular, the charge density applied to the nerve by the electrical signal is below the predetermined threshold for each and every phase of the electrical signal.

The predetermined threshold is defined as the minimum charge density per phase required to produce sympatho-excitation responses that are associated with sympatho-excitation in the effector. The predetermined threshold is denoted herein as '$\tau$'.

In some embodiments, the predetermined threshold may be a predetermined afferent threshold. The predetermined afferent threshold is determined using the electrode configuration in FIG. 5A, as is further discussed below. The predetermined afferent threshold is denoted herein as '$\tau_A$'.

In some embodiments, the predetermined threshold may be a predetermined efferent threshold. The predetermined efferent threshold is determined using the electrode configuration in FIG. 5B, as is further discussed below. The predetermined efferent threshold is denoted herein as '$\tau_E$'.

It is known in the art that the predetermined efferent threshold $\tau_E$ is lower than the predetermined afferent threshold $\tau_A$. Thus, in some embodiments, the charge density per phase applied to nerve according to the invention by the electrical signal may be above the predetermined efferent threshold $\tau_E$ and below the predetermined afferent threshold $\tau_A$.

In embodiments where the effector is the heart, the predetermined threshold may be defined as the minimum charge density per phase required to produce a cardiac response that is associated with cardiac sympatho-excitation, and the response comprises: a positive chronotropic response (e.g. increase in heart rate), a positive dromotropic response, a positive lusitropic response and/or a positive inotropic response.

In embodiments where the effector is the foregut, the predetermined threshold may be defined as the minimum charge density per phase required to produce responses that are associated with sympatho-excitation, e.g. increase in blood pressure, increase in heart rate, and/or increase in myocardial contractility.

Charge per phase applied to the nerve by the electrical signal is defined as the integral of the current over one phase (e.g. over one phase of the biphasic pulse in the case of a charge-balanced biphasic pulse). Thus, charge density per phase applied to the nerve by the electrical signal is the charge per phase per unit of contact area between at least one neural interfacing element (e.g. an electrode) and the nerve, and also the integral of the current density over one phase of the signal waveform. Put another way, the charge density per phase applied to the nerve by the electrical signal is the charge per phase applied to the nerve by the electrical signal divided by the contact area between the at least one neural interfacing element and the nerve.

The electrical parameters for the signal of the predetermined threshold are typically chosen such that for each individual, there was minimal change in a physiological parameter.

For example, in embodiments where the effector is the heart, the physiological parameter to be measured for determining the threshold may be heart rate. In such embodiments, the predetermined threshold is chosen such that for each individual, there is minimal change in the heart rate during the on-phase of the signal application, but that with one additional step up in one electrical parameter (e.g. current intensity), tachycardia would be reproducibly evoked.

For example, in embodiments where the target is the foregut, the physiological parameter to be measured for determining the threshold may be systemic blood pressure, heart rate and/or myocardial contractility. In such embodiments, the predetermined threshold is chosen such that for each individual, there is minimal change in the systemic blood pressure, heart rate and/or myocardial contractility during the on-phase of the signal application, but that with one additional step up in one electrical parameter (e.g. current intensity), increase in systemic blood pressure, increase in heart rate and/or increase in myocardial contractility would be reproducibly evoked.

The predetermined threshold may vary according to the user of the device. The threshold may vary by one or more of: age, sex and general health of the user. Thus, the predetermined threshold may be a value that is determined in the subject who will be receiving a signal to modulate the neural activity of the as described herein, and so the predetermined threshold would be specific to the subject.

Alternatively, the predetermined threshold may be a fixed value. For example, the predetermined threshold may be an average that has been determined across a group of subjects. The group of subjects may be age-specific, gender-specific, and/or disorder-specific. For example, subjects who suffer from or are at risk of a particular cardiac disorder, as described herein.

The predetermined threshold may be ≤80 μC/cm²/phase. For example, the predetermined threshold may be 5 μC/cm²/phase, 10 μC/cm²/phase, 15 μC/cm²/phase, 20 μC/cm²/phase, 25 μC/cm²/phase, 30 μC/cm²/phase, 35 μC/cm²/phase, 40 μC/cm²/phase, 45 μC/cm²/phase, 50 μC/cm²/phase, 55 μC/cm²/phase, 60 μC/cm²/phase, 75 μC/cm²/phase, 80 μC/cm²/phase, or any value between.

In some embodiments, the electrical signal used with the invention is configured to have a charge density per phase of between 0.1τ and 0.9τ. For example, the charge density per phase to be applied may be: between 0.2τ and 0.8τ, between 0.3τ and 0.7τ, or between 0.4τ and 0.6τ. In other embodiments, the charge density per phase to be applied may be: ≤0.1τ, ≤0.2τ, ≤0.3τ, ≤0.4τ, ≤0.5τ, ≤0.6τ, ≤0.7τ, ≤0.8τ, or ≤0.9τ. Alternatively or additionally, the charge density per phase to be applied may be: ≥0.1τ, ≥0.2τ, ≥0.3τ, ≥0.4τ, ≥0.5τ, ≥0.6τ, ≥0.7τ, ≥0.8τ, or ≥0.9τ.

Methods for Determining the Threshold

As explained herein, the predetermined threshold is determined by applying an electrical signal to the nerve with a particular electrode configuration.

Examples of electrode configurations for determining the predetermined threshold are shown in Reference [13] (i.e., the 'cardiac' and 'epilepsy' electrode configurations). In particular, the 'epilepsy' electrode configuration, which uses two electrodes with the cathode cephalad to the anode, determines the predetermined afferent threshold TA. The 'cardiac' electrode configuration, which uses two electrodes arranged with the anode cephalad to the cathode, determines the predetermined efferent threshold $\tau_E$.

Figure 5A:
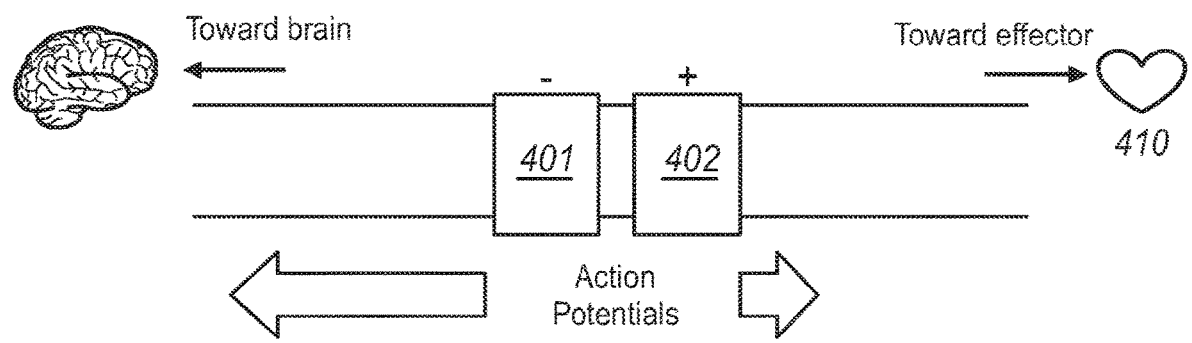
FIGS. 5A-5B are schematic diagrams showing some electrode configurations for determining the predetermined threshold.
Figure 5B:
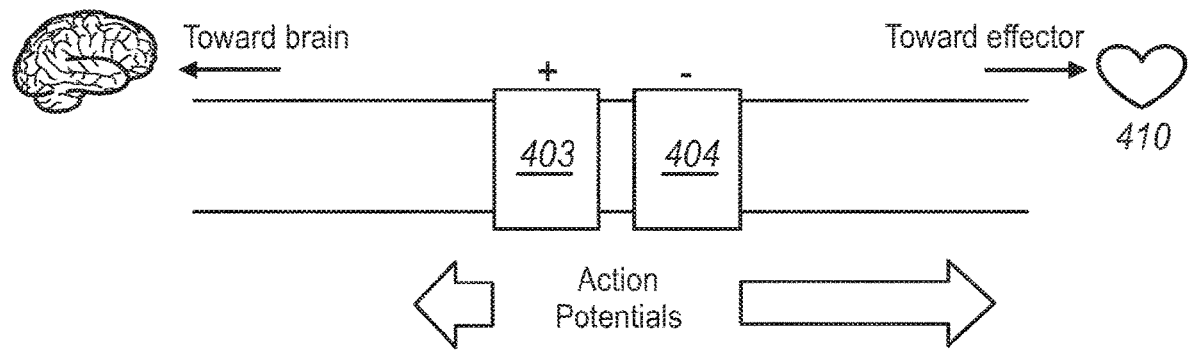

The 'epilepsy' configuration, which is referred to herein as the 'first electrode configuration' is shown in FIG. 5A. The 'cardiac' configuration, which is referred to herein as the 'second electrode configuration' is shown in FIG. 5B.

Without wishing to be bound by theory, the predetermined afferent threshold $\tau_A$ may be determined using at least two neural interfacing elements (e.g. electrodes) arranged in the configuration shown in FIG. 5A by inciting action potentials that preferentially propagate away from an effector (i.e. in the afferent direction).

Referring to FIG. 5A, a first electrode 401 is positioned along the nerve axis adjacent to the second reference electrode 402, and arranged such that the second reference electrode 402 is closer to the effector 410 along the nerve axis than the first reference electrode 403.

When an electrical signal is applied to the first electrode 401 such that it becomes negatively charged (cathode) a depolarization of the axon occurs generating an action potential, and when an electrical signal is applied to the second electrode 402 such that it becomes positively charged (anode), a hyperpolarization of the axon can occur inhibiting the propagation of action potentials past the anode. Under optimized conditions, the propagation of the action potentials generated in the nerve is biased in the afferent direction.

Without wishing to be bound by theory, the predetermined efferent threshold $\tau_E$ may be determined using at least two neural interfacing elements (e.g. electrodes) arranged in the configuration shown in FIG. 5B by inciting action potentials that preferentially propagate towards an effector (i.e. in the efferent direction).

Referring to FIG. 5B, a first electrode 403 is positioned along the nerve axis adjacent to the second electrode 404, and arranged such that the second electrode 404 is closer to the effector 410 along the nerve axis than the first electrode 403. Put another way, the first electrode is rostral along the axis of the nerve to the second electrode.

When an electrical signal is applied to the second electrode 404 such that it becomes negatively charged (cathode) a depolarization of the axon occurs generating an action potential, and when an electrical signal is applied to the first electrode 403 such that it becomes positively charged (anode), a hyperpolarization of the axon can occur inhibiting the propagation of action potentials past the anode. Under optimized conditions, the propagation of the action potentials in the nerve is biased in the efferent direction.

In an example, the predetermined threshold may be determined in a subject by applying to the nerve electrical signals with increasing average current intensity (mA) at small intervals (e.g. increments of 0.1 mA), each for a constant duration (e.g. 2 min), at a constant frequency (e.g. 1 Hz), and with a constant area of contact between the at least two neural interfacing elements and the nerve (e.g. 1 mm$^2$). Then, identifying the minimum average current intensity (e.g. 1 mA) at which a response in the heart is produced. The response may be indicated by statistically significant changes in one or more responses of the heart, as described above. Examples of the small intervals of the average current intensity that may be tested are 0.05 mA, 0.1 mA, 0.2 mA, or 0.5 mA.

By way of a further example, the predetermined threshold may be determined in a subject by applying to the nerve electrical signals with increasing frequency (Hz) at small intervals (e.g. increments of 0.1 Hz), each for a constant duration (e.g. 2 min), at a constant average current intensity (e.g. 1 mA), and with a constant area of contact between the at least two neural interfacing elements and the nerve (e.g. 1 mm$^2$). Then, identifying the maximum frequency (e.g. 1 Hz) at which a response in the heart is produced. The response may be indicated by statistically significant changes in one or more responses of the heart, as described above. Examples of the small intervals of the frequency that may be tested are 0.05 Hz, 0.1 Hz, 0.2 Hz, 0.5 Hz, or 1 Hz.

By way of a further example, the predetermined threshold may be determined in a subject by applying to the nerve electrical signals with increasing the duration (e.g. increments of 10 sec), at a constant average current intensity (e.g. 1 mA), at a constant frequency (e.g. 1 Hz) and with a constant area of contact between the at least two neural interfacing elements and the nerve (e.g. 1 mm$^2$). Then, identifying the minimum duration (e.g. 2 min) at which a response in the heart is produced. The response may be indicated by statistically significant changes in one or more responses of the heart, as described above. Examples of the duration that may be tested are <10 sec, <30 sec, <1 min, <2 min, or <5 min. The duration tested may be, for example, 1 sec, 2 sec, 5 sec, 10 sec, or 15 sec.

It would be of course understood in the art that the electrical signal applied to the nerve for determining the predetermined threshold would be within clinical safety margins (e.g. suitable for maintaining nerve signaling function, suitable for maintaining nerve integrity, and suitable for maintaining the safety of the subject). The electrical parameters within the clinical safety margin would typically be determined by pre-clinical studies. For example, the frequency of the signal is not higher than 200 Hz, 150 Hz, 100 Hz, or 50 Hz. For example, the average current intensity of the signal is not larger than 50 mA, 25 mA, or 10 mA. For example, the duration is not more than 24 h, 10 h, 5 h, or 1 h.

Neural Interfacing Elements

As mentioned above, the invention involves modulating a nerve by inciting action potentials that propagate preferentially away from an effector, towards a ganglion (i.e. in the afferent direction). This may be achieved using at least two neural interfacing elements, as discussed above and in reference [20]. Thus, a system of the invention preferably comprises at least two neural interfacing elements for modulation of the neural activity in a nerve according of the invention.

The at least two neural interfacing elements of the system are configured to apply the electrical signals to a nerve, or a part thereof. However, the skilled person will appreciate that electrical signals are just one way of implementing the invention.

The neural interfacing elements are preferably electrodes (e.g. electrode 109, 401, 402). Each neural interfacing element may comprise one or more conducting materials (not limited to non-reactive metals, graphene and/or conductive polymers). Each neural interfacing element defines one contact pad (e.g. an electrical contact pad) between the system of the invention and the nerve. Thus, one neural interfacing element may be a single unipolar electrode. Two neural interfacing elements may be two unipolar electrodes, also referred to in the art as a bipolar electrode. Three neural interfacing elements may be three unipolar electrodes, also referred to in the art as a tripolar electrode, etc.

To incite action potentials that propagate preferentially away from an effector, towards a ganglion (i.e. in the afferent direction), the at least two neural interfacing elements are arranged in the configuration shown in FIG. 5A.

Referring to FIG. 5A, a first electrode 401 is positioned along the nerve axis adjacent to the second reference electrode 402, and arranged such that the second reference electrode 402 is closer to the effector 410 along the nerve axis than the first reference electrode 403.

When an electrical signal is applied to the first electrode 401 such that it becomes negatively charged (cathode) a depolarization of the axon occurs generating an action potential, and when an electrical signal is applied to the second electrode 402 such that it becomes positively charged (anode), a hyperpolarization of the axon can occur inhibiting the propagation of action potentials past the anode. Under optimized conditions, the propagation of the action potentials generated in the nerve is biased in the afferent direction.

Effectors suitable for use with the first electrode configuration of FIG. 5A include the heart, and the foregut. Any of the signal application sites discussed above are suitable for targeting one of these effectors using the first electrode configuration.

In some embodiments, the first electrode configuration of FIG. 5A may be adapted to improve the biasing of action potentials such that the action potentials travel preferentially in the afferent direction. These embodiments are shown in FIGS. 6A-6C.

Figure 6A:
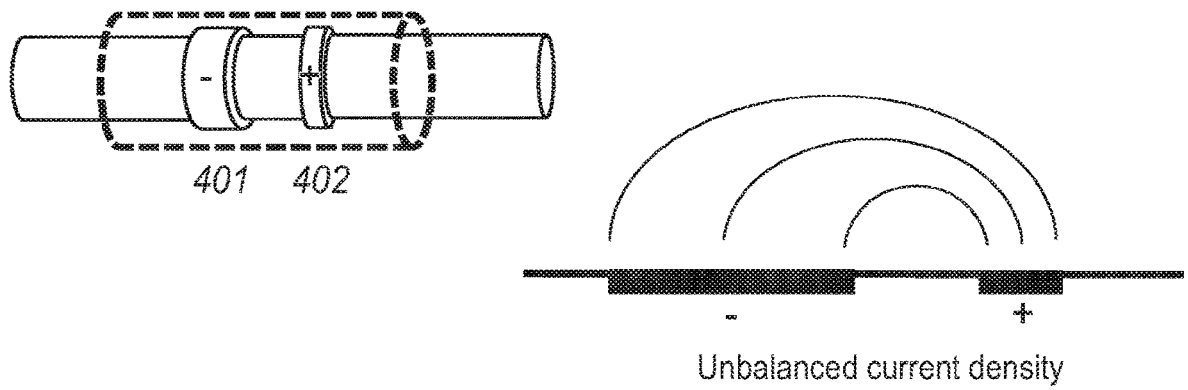
FIGS. 6A, 6B, and 6C are schematic diagrams showing some electrode configurations for inciting action potentials preferentially in a particular direction.
Figure 6B:
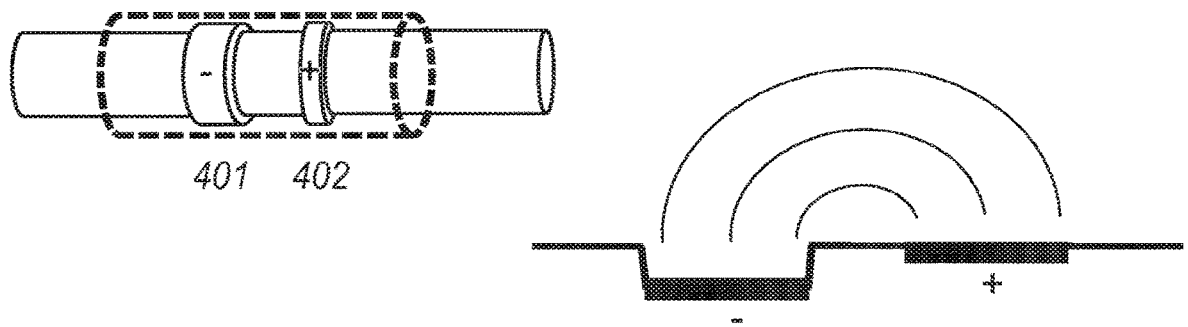
Figure 6C:
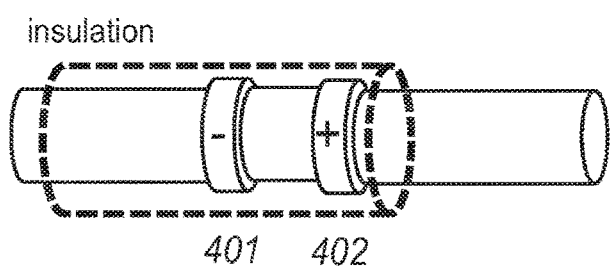

In some embodiments, as shown in FIG. 6A, the surface area of the first electrode 401 is different to the surface area of the second electrode 402. In particular, the surface area of the first electrode 401 is adapted to be larger than the surface area of the second electrode 402 to concentrate charge density under the second electrode 402, thus strengthening the hyperpolarization of the nerve without increased energy requirements.

For cuff type electrodes that fully circumvent the nerve, the size of this surface area can be calculated by multiplying $\pi$ (i.e. 3.14159) by the internal diameter and width the electrode (i.e. the first electrode 401 or the second electrode 402). Since the internal diameter of the first electrode 401 and the second electrode 402 is fixed by the diameter of the nerve, the surface area of each of the first electrode 401 and the second electrode 402 which is contactable with the nerve is adjusted by changing the width of the electrode. The width of each of the first electrode 401 and the second electrode 402 being defined as the distance the electrode spans along the longitudinal axis of the nerve. Thus, in such embodiments, the width of the first electrode 401 is greater than the width of the second electrode 402. For example, the width of the first electrode 401 may be at least twice the width of the second electrode 402.

In such embodiments, the width of the first electrode 401 may also be less than or equal to five times the width of the second electrode 402. This is to avoid stimulating additional action potentials under the second electrode 402.

Thus, in such embodiments, the width of the second electrode 402 may be set at any value between the upper and lower limits described above. For example, the width of the first electrode 401 may be 2, 2.5, 3.0, 3.5, 4.0, 4.5 or 5.0 times the width of the second electrode 402.

In other embodiments, as shown in FIG. 6B, one of the first electrode 401 and second electrode 402 may be recessed away from the nerve, as discussed in [24]. In particular, the first electrode 401 is radially recessed away from the nerve to reduce extracellular potential at the nerve interfacing the second electrode 401 compared to the extracellular potential at the nerve interfacing the second electrode 402 which is not recessed away.

In such embodiments, the first electrode configuration may include insulation circumventing the first electrode 401 and second electrode 402. The insulation circumventing the second electrode 402 may be thinner than the insulation circumventing the first electrode 401. This may decrease the impedance of an electrical return path outside of the insulation compared to at the neural interface, increasing the possibility of forming virtual anodes and cathodes. The radially recessed second electrode 402 has a reduced extracellular potential compared to that of first electrode 401 which reduces the formation of a virtual cathode between the first electrode configuration and the brain, allowing directionality to be conveyed via a virtual anode proximal between the first electrode configuration and the effector.

In further embodiments, as shown in FIG. 6C, the insulation circumventing the first electrode 401 and second electrode 402 may be asymmetric, see, for example [24,25]. In particular, the surface area of the insulation contactable with the nerve either side of the first electrode arrangement is unequal such that the surface area adjacent the first electrode 401 is greater than the surface area adjacent the second electrode 402. In other words, the neural interface comprises first and second insulation regions on either side of the electrodes which is situated off-center to the interface such that the insulation regions have different lengths.

In such embodiment, the asymmetry of the insulation has the effect of reducing the generation of virtual anodes and virtual cathodes which negate directionality.

It will be appreciated by a person skilled in the art that the embodiments of FIGS. 6A, 6B and 6C may be combined in any way to improve the biasing of action potentials such that the action potentials travel preferentially in the afferent direction. For example, the imbalanced surface area electrodes of FIG. 6A is preferably circumvented by the asymmetric insulation of FIG. 6C.

Other suitable electrode configurations for inciting action potentials that propagate preferentially away from the effector, towards a ganglion (i.e. in the afferent direction) are discussed in Reference [11]. Thus, in some embodiments, only one neural interfacing element (e.g. one electrode) may be required. In other embodiments, at least three neural interfacing elements (e.g. three electrodes) may be used.

In some embodiments, one of the electrode configurations described above is positioned on a neural interface (e.g. neural interface 108). In such embodiments, the neural interface is positioned on the nerve on or around the nerve at one of the sites previously discussed (i.e. those shown in FIG. 3 and FIG. 4) suitable for the effector. Thus, for example, there may be two, three, four, or more neural interfacing elements for applying a signal at a site. In such embodiments, the neural interfacing elements may be positioned on the neural interface such that, in use, the neural interfacing elements are located transversely along the axis of the nerve.

The plurality of electrodes at a single site may be insulated from one another by a non-conductive biocompatible material. To this end, the neural interface may comprise a non-conductive biocompatible material which is spaced transversely along the nerve when the device is in use.

In some embodiments, the at least two neural interfacing elements used to apply a signal to the nerve to incite action potentials that propagate preferentially away from the effector, towards a ganglion (i.e. in the afferent direction) for modulating neural activity in the nerve, may also be used for determining the predetermined threshold.

In some embodiments, the at least two neural interfacing elements may also be used for determining the predetermined afferent threshold $\tau_A$. In such embodiments, the at least two neural interfacing elements may be arranged according to the 'first electrode configuration' shown in FIG. 5A. Using this configuration, the predetermined afferent threshold $\tau_A$ is determined according to one of the methods discussed above. Then, a signal is applied to the nerve below the predetermined threshold for modulating neural activity in the nerve. Suitable electrical parameters for this signal are discussed in detail below.

In some embodiments, the at least two neural interfacing elements may also be used for determining the predetermined efferent threshold $\tau_E$. In such embodiments, the at least two neural interfacing elements may be arranged according to the 'second electrode configuration' shown in FIG. 5B. Using this configuration, the predetermined efferent threshold $\tau_E$ is determined according to one of the methods discussed above. Then, to apply a signal to the nerve which generates action potentials that propagate preferentially away from the effector, towards a ganglion, the polarity of each of the electrodes is switched such that the cathode becomes an anode, and the anode becomes a cathode, where switching may involve applying a different signal to the electrodes via a signal generator. The electrodes are consequently in the first electrode configuration shown in FIG. 5A. Using this configuration, the electrodes can apply a signal to the nerve to incite action potentials that propagate preferentially away from the effector, towards a ganglion (i.e. in the afferent direction) for modulating neural activity in the nerve. Suitable electrical parameters for this signal are discussed in detail below.

In some embodiments, the system may comprise a plurality of neural interfaces. For example, there may be two, three or more neural interfaces.

The plurality of neural interfaces may be used for applying a signal to multiple sites on the nerve, each neural interface corresponding to a site on the nerve and comprising one of the electrode configurations described above. In some embodiments, the sites may be each be located at a different interganglionic branches of the nerve, or at an interganglionic branch and between a ganglion and an effector. In other words, there may be a plurality of neural interfaces, each located at different interganglionic branches of the nerve, or at an interganglionic branch and between a ganglion and an effector. In other embodiments, there may be one or more sites for applying a signal at each interganglionic branch of the nerve and/or between a ganglion and the effector. In other words, there may be a plurality of neural interfaces located a single interganglionic branch of the nerve, or between a ganglion and an effector. A combination of the embodiments above is also possible. The site for applying a signal can be at any of the interganglionic branches at the left and/or right sympathetic chains.

Alternatively or additionally, one of the plurality of neural interfaces may be used for determining the predetermined threshold. In such embodiments, the neural interface may comprise the first electrode configuration shown in FIG. 5A or the second electrode configuration as shown in FIG. 5B. In some embodiments, the neural interface for determining the predetermined threshold may be located at a different interganglionic branch of the nerve than the neural interface for modulation of neural activity. In other embodiments, neural interface for determining the predetermined threshold may be located at an interganglionic branch whilst the neural interface for modulation is located between a ganglion and an effector, or vice versa. In other embodiments, neural interface for determining the predetermined threshold may be located at the same interganglionic branch of the nerve, or at the same location between a ganglion and an effector, as the neural interface for modulation of neural activity.

Figure 7A:
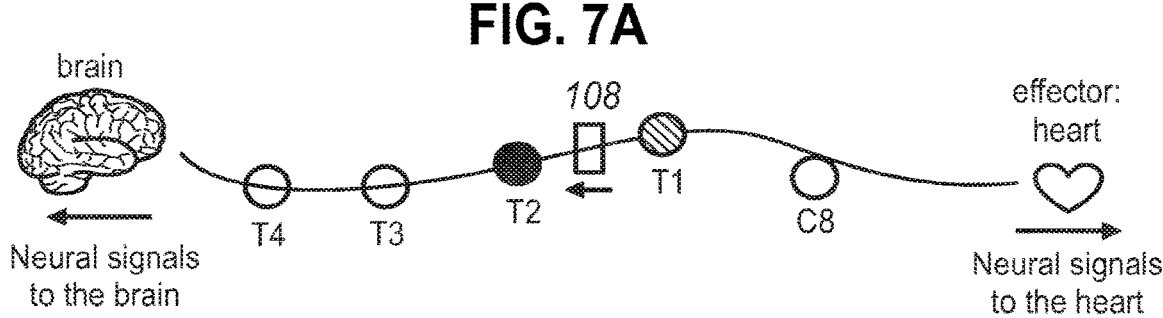
FIGS. 7A-7B are schematic diagrams depicting neural interface arrangements on the sympathetic chain.

In a first exemplary embodiment, as shown in FIG. 7A, a neural interface 108 at a site on the branch between T1-T2 ganglia. In this embodiment, the neural interface 108 may be suitable for modulating neural activity of the nerve only, or may be suitable for modulating neural activity of the nerve and for determining the predetermined threshold, as discussed above. In this first exemplary embodiment, the effector is the heart, and the action potentials propagate preferentially towards the T2 ganglion (i.e. in the afferent direction).

Figure 7B:
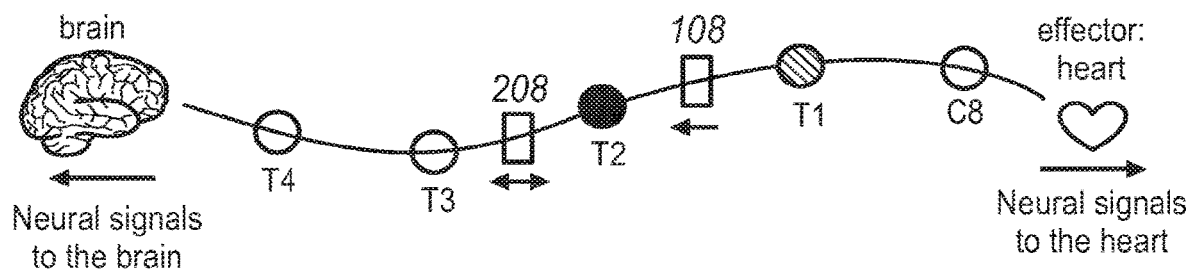

In a second exemplary embodiment, shown in FIG. 7B, a first neural interface 108 is at a first site between T1-T2 ganglia, the first neural interface suitable for modulating neural activity of the nerve. There is also a second neural interface 208 at a second site between T2-T3 ganglia for determining the predetermined threshold. In this second exemplary embodiment, the effector is the heart, and the action potentials for modulation of neural activity propagate preferentially towards the T2 ganglion (i.e. in the afferent direction).

Figure 8A:
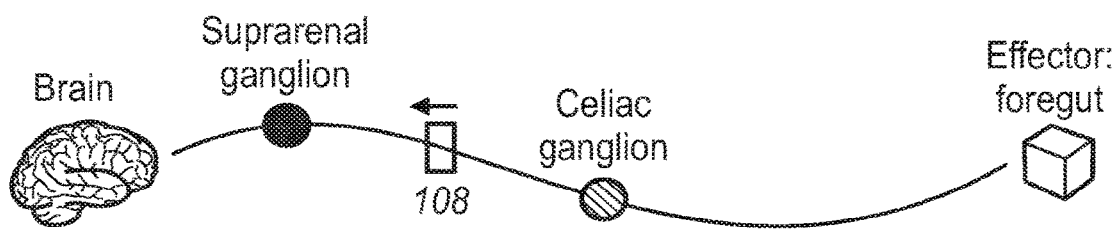
FIGS. 8A-8B are schematic diagrams depicting neural interface arrangements at the GSN branches.

In a third exemplary embodiment, as shown in FIG. 8A, a neural interface 108 is at a site on the branch between the suprarenal ganglion and the celiac ganglion. In this embodiment, the neural interface 108 may be suitable for modulating neural activity of the nerve only. In this third exemplary embodiment, the effector is the foregut, and the action potentials for modulation of neural activity propagate preferentially towards the suprarenal ganglion (i.e. in the afferent direction).

Figure 8B:
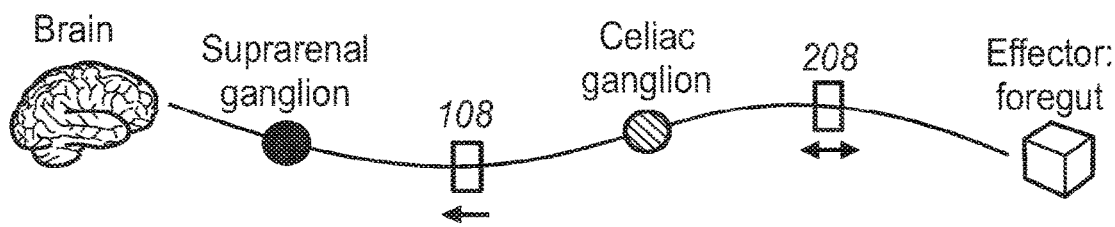

In a fourth exemplary embodiment, shown in FIG. 8B, a first neural interface 108 is at a first site between the suprarenal ganglion and the celiac ganglion, the first neural interface suitable for modulating neural activity of the nerve. There is also a second neural interface 208 at a second site between the celiac ganglion and the foregut for determining the predetermined threshold. In this fourth exemplary embodiment, the effector is the foregut, and the action potentials for modulation of neural activity propagate preferentially towards the suprarenal ganglion (i.e. in the afferent direction).

Typically, the electrode applies the electrical signal by exerting an electrical field across the nerve bundle, and hence applying the electrical signal to many nerve fibers within the bundle. This generates multiple action potentials in each nerve fiber, and the combination of these action potentials may be called a compound action potential.

In some embodiments, the at least one neural interface and/or at least one electrode is configured to at least partially circumvent the nerve. In some embodiments, the at least one neural interface and/or at least one electrode is configured to fully circumvent the nerve, which may form a cuff.

Electrodes may be shaped as one of: a rectangle, an oval, an ellipsoid, a rod, a straight wire, a curved wire, a helically wound wire, a barb, a hook, or a cuff. In addition to the one or more electrodes which, in use, is located on, or around a nerve according to the invention, there may also be a larger indifferent electrode placed in the adjacent tissue.

Electrodes may have a surface area in contact with the nerve between 0.5 mm$^2$ and 5 mm$^2$, preferably between 0.75 mm$^2$ and 1 mm$^2$.

Figure 9:
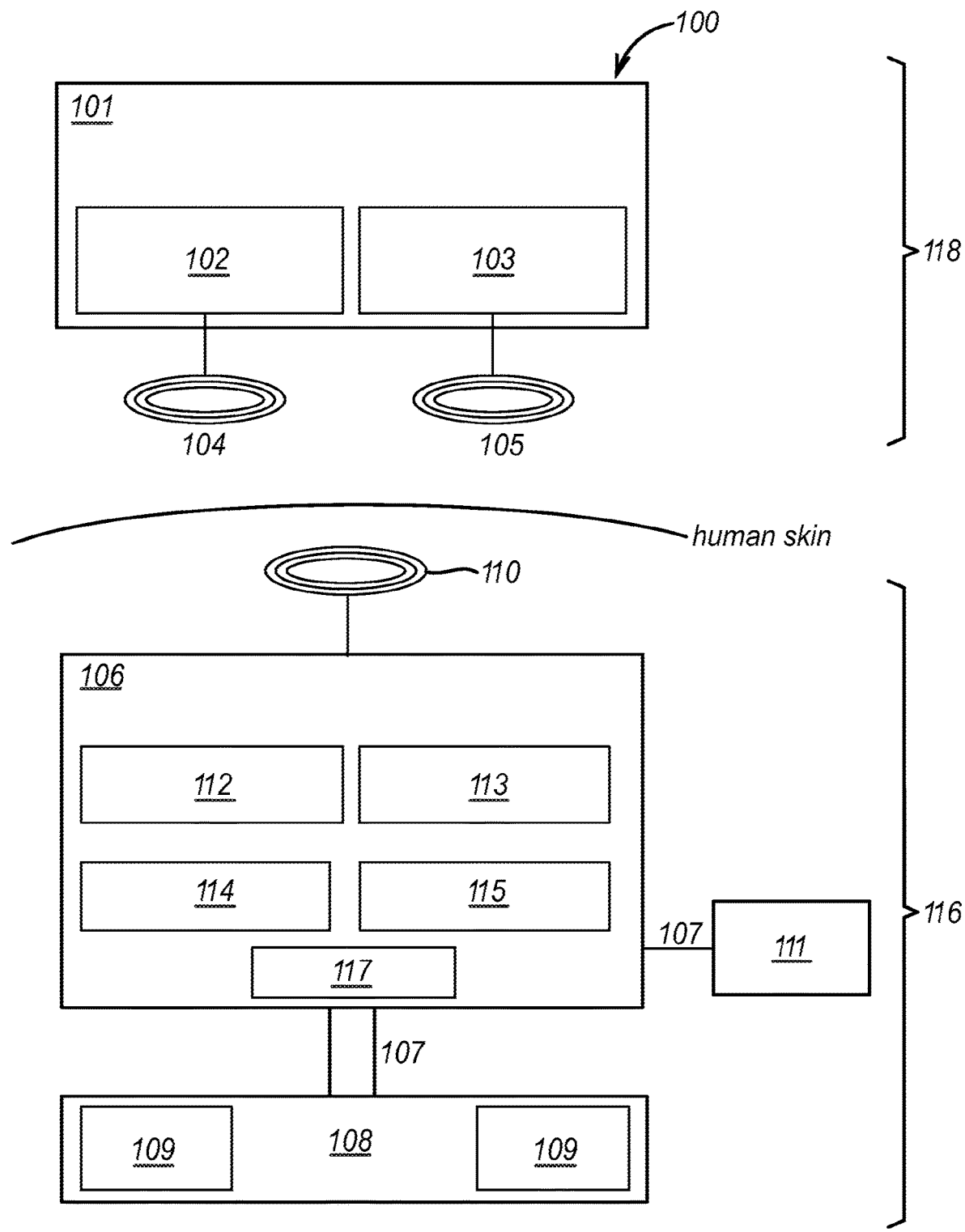
FIG. 9 is a block diagram illustrating elements of a system for performing electrical neuromodulation in a sympathetic nerve according to the present invention.

The electrodes may be coupled to an implantable device 106 of system 116 via electrical leads 107 (see FIG. 9). Alternatively, implantable device 106 may be directly integrated with the electrodes 109 without leads. In any case, implantable device 106 may comprise DC current blocking output circuits, optionally based on capacitors and/or inductors, on all output channels (e.g. outputs to the electrodes 109, or physiological sensor 111).

In some embodiments, electrodes may be used for recording neural activity of the sympathetic chain. These recording electrodes may be positioned on a neural interface with the at least two neural interfacing elements. Alternatively, recording electrodes may be positioned on a separate neural interface from the at least two neural. For example, in the embodiment as described in FIG. 6B, the neural interface between T2-T3 may have at least one recording electrode for recording neural activity of the sympathetic chain. Recording electrodes are discussed further below.

A System According to the Invention

The invention involves applying at least one electrical signal via the at least two neural interfacing elements discussed above placed in signaling contact with a nerve according to the invention. The signal is an electrical signal, which may be, for example, a voltage or current signal.

A system 116 according to the invention comprises a device which may be implantable (e.g. implantable device 106 of FIG. 9). The implantable device comprises at least two neural interfacing elements (e.g. electrode 109), suitable for placement on, or around a nerve according to the invention. The system may also comprises a processor (e.g. microprocessor 113) coupled to the at least two neural interfacing elements.

The system 116 may comprise an implantable device 106 which may comprise at least one signal generator 117. The signal generator 117 may comprise a voltage source or a current source, configured to apply a voltage signal or a current signal respectively. The various components of the system are preferably part of a single physical device, either sharing a common housing or being a physically separated collection of interconnected components connected by electrical leads (e.g. leads 107). As an alternative, however, the invention may use a system in which the components are physically separate, and communicate wirelessly. Thus, for instance, the at least two neural interfacing elements (e.g. electrode 109) and the implantable device (e.g. implantable device 106) can be part of a unitary device, or together may form a system (e.g. system 116). In both cases, further components may also be present to form a larger system (e.g. system 100).

Signal Parameters

In the present invention, a signal generator 117, such as a voltage or current source, is configured to apply at least one electrical signal to a nerve according to the invention which has a charge density per phase below the predetermined threshold to modulate neural activity in the nerve.

In some embodiments, the electrical signal used with the invention may be defined by the combination of the predetermined threshold and one or more signal parameters. The predetermined threshold, in turn, may be defined by the combination of the charge density per phase and the one or more signal parameters (e.g. waveform, frequency, and amplitude).

The relationship between the charge density per phase applied to the nerve by the electrical signal and the signal parameters is discussed above. The skilled person is therefore able to calculate the charge density per phase supplied by a particular set of signal parameters. Accordingly, the charge density per phase applied to the nerve by the electrical signal may be varied by altering one or more signal parameters, e.g. waveform, frequency, and amplitude.

Waveform

The electrical signal comprises a direct current (DC) waveform, or an alternating current (AC) waveform, or both a DC and an AC waveform.

In some embodiments, the waveform is a charge-balanced DC waveform with a constant average current intensity. As used herein, "charge-balanced" in relation to a DC current is taken to mean that the positive or negative charge applied to the nerve as a result of a DC current being applied is balanced by the introduction of the opposite charge in order to achieve overall (net) neutrality. The initial charge applied is referred to herein as the "charge phase" and the opposite charge is referred to herein as a "recharge phase". The charge phase plus the recharge phase represent one phase of the signal, which may be repeated to form the charge-balanced DC waveform. The charge phase may have a duration between 2 and 5 times that of the recharge phase.

In other embodiments, the AC waveform comprises one or more pulse trains, each with a defined pulse width. The pulses are preferably square pulses. Other pulse waveforms such as sawtooth, sinusoidal, triangular, trapezoidal, quasi-trapezodial or complex waveforms may also be used with the invention. In certain embodiments, quasitrapezodial waveforms are particularly useful, e.g. when applying the electrical signal for long durations (e.g. >0.5 ms).

The pulse width may be ≤2 ms, preferably between 0.01 and 2 ms (including, if applicable, both positive and negative phases of the pulse, in the case of a charge-balanced biphasic pulse). For example, the pulse width may be: ≤0.05 ms, ≤0.1 ms, ≤0.2 ms, ≤0.5 ms, ≤1 ms, ≤1.5 ms, or ≤2 ms. Alternatively or additionally, the pulse width may be: ≥0.05 ms, ≥0.1 ms, ≥0.2 ms, ≥0.5 ms, ≥1 ms, or ≥1.5 ms. The pulse width may additionally be limited by the frequency.

The pulses may be biphasic pulses. The term "biphasic" refers to a signal which applies to the nerve over time both a positive and negative charge. The biphasic pulses are preferably charge-balanced. The term "charge-balanced" in relation to a pulse train is taken to mean that the positive charge and negative charge applied by the signal over the pulse duration is equal. Alternatively, the pulses may be monophasic pulses.

The electrical signal may be a charge-balanced signal. A charge-balanced signal refers to a signal which, over a period of time, applies equal amounts (or thereabouts) of positive and negative charge to the nerve.

In some embodiments, the pulses may be charge-balanced. The charge-balanced pulses may be symmetric or asymmetric. A symmetric pulse is a pulse where the waveform when applying a positive charge to the nerve is symmetrical to the waveform when applying a negative charge to the nerve. An asymmetric pulse is a pulse where the waveform when applying a positive charge to the nerve is not symmetrical with the waveform when applying a negative charge to the nerve.

In some embodiments, the waveform is a pulse train with charge-balanced biphasic pulses, e.g. square pulses.

Frequency

Frequency is defined as the reciprocal of the phase duration (i.e. 1/phase). The frequency for use with the invention is less than 30 Hz, and preferably less than 10 Hz such that action potentials in the nerve are stimulated (rather than inhibited). For example, the frequency may be between 0.01 and 10 Hz, or between 0.01 and 5 Hz, or between 0.01 and 2 Hz. In other examples, the frequency may be: ≤1 Hz, ≤2 Hz, ≤3 Hz, ≤4 Hz, ≤5 Hz, ≤6 Hz, ≤7 Hz, ≤8 Hz, or ≤9 Hz. Additionally or alternatively, the frequency may be: ≥1 Hz, ≥2 Hz, ≥3 Hz, ≥4 Hz, ≥5 Hz, ≥6 Hz, ≥7 Hz, ≥8 Hz, or ≥9 Hz.

In some embodiments where the waveform is a charge-balanced DC waveform, the frequency represents the number of charge and recharge phases per second. For example, a frequency of 1 to 10 Hz results in a number of charge and recharge phases between 1 and 10.

In some embodiments where the waveform is a pulse train, the pulses are applied at intervals according to the above-mentioned frequencies. For example, a frequency of 1 to 10 Hz results in a pulse interval between 1 pulse per second and 10 pulses per second, within a given pulse train.

Amplitude

For the purpose of the invention, and in keeping with the art, the amplitude is referred to herein in terms of average current intensity. An electrical signal suitable for the invention has an average current intensity of less than 10 mA, preferably between 10 µA and 10 mA.

In embodiments where the waveform is a pulse train with charge-balanced biphasic square pulses, the average current intensity may be between 500 µA to 10 mA. For example, the average current intensity may be: ≤1 mA, ≤2 mA, ≤3 mA, ≤4 mA, ≤5 mA, ≤6 mA, ≤7 mA, ≤8 mA, ≤9 mA, or ≤10 mA. Additionally or alternatively, the average current intensity may be: ≥1 mA, ≥2 mA, ≥3 mA, ≥4 mA, ≥5 mA, ≥6 mA, ≥7 mA, ≥8 mA, or ≥9 mA.

In embodiments where the waveform is a DC waveform with a constant average current intensity, the average current intensity may be between 10 µA to 500 µA. For example, the average current intensity may be: ≤50 mA, ≤100 mA, ≤150 mA, ≤200 mA, ≤250 mA, ≤300 mA, ≤350 mA, ≤400 mA, 450 mA or ≤500 mA. Alternatively or additionally, the amplitude may be: ≥10 mA, ≥50 mA, ≥100 mA, ≥150 mA, ≥200 mA, ≥250 mA, ≥300 mA, ≥350 mA, ≥400 mA or ≥450 mA.

The signal generator 117 may be pre-programmed to apply one or more signals with signal parameters falling within the ranges discussed above. Alternatively, the signal generator 117 may be controllable to adjust one or more of the signal parameters discussed above while ensuring that the charge density per phase applied is below the predetermined threshold. Control may be open loop, wherein the operator of the implantable device 106 may configure the signal generator using an external controller (e.g. controller 101), and warnings may be issued to the operator if the charge density per phase applied is not below the predetermined threshold. Control may alternatively or additionally be closed loop, wherein signal generator modifies the signal parameters in response to one or more responses in the effector. Open loop and closed loop control of signal parameters is further described below.

The signal may be applied continuously, or periodically (i.e. for a specific duration), as is further discussed below.

It will be appreciated by the skilled person that the signal parameters of an applied electrical signal necessary to achieve the intended modulation of the neural activity will depend upon the positioning of the electrode and the associated electrophysiological characteristics (e.g. impedance). It is within the ability of the skilled person to determine the appropriate variations in signal parameters for achieving the intended modulation of the neural activity in a given subject.

Electrical signals applied according to the invention are ideally non-destructive. As used herein, a "non-destructive signal" is a signal that, when applied, does not irreversibly damage the underlying neural signal conduction ability of the nerve. That is, application of a non-destructive signal maintains the ability of the nerve or fibers thereof, or other nerve tissue to which the signal is applied, to conduct action potentials when application of the signal ceases, even if that conduction is in practice artificially increased as a result of application of the non-destructive signal.

It would be of course understood in the art that the electrical signals applied to the nerve would be within clinical safety margins (e.g. suitable for maintaining nerve signaling function, suitable for maintaining nerve integrity, and suitable for maintaining the safety of the subject). The electrical parameters within the clinical safety margin would typically be determined by pre-clinical studies. For example, the frequency of the signal is not higher than 200 Hz, 150 Hz, 100 Hz, or 50 Hz. For example, the average current intensity of the signal is not larger than 50 mA, 25 mA, or 10 mA. For example, the duration is not more than 24 h, 10 h, 5 h, or 1 h.

Microprocessor

The implantable device 106, may comprise a processor, for example microprocessor 113. Microprocessor 113 may be responsible for triggering the beginning and/or end of the signals applied to a nerve according to the invention by the at least two neural interfacing elements. Optionally, microprocessor 113 may also be responsible for generating and/or controlling the signal parameters of the signal such that the charge density per phase applied to the nerve is below the predetermined threshold.

Microprocessor 113 may be configured to operate in an open-loop fashion, wherein a pre-defined signal (e.g. as described above) is applied to the nerve at a given periodicity (or continuously) and for a given duration (or indefinitely) with or without an external trigger, and without any control or feedback mechanism. Alternatively, microprocessor 113 may be configured to operate in a closed-loop fashion, wherein a signal is applied based on a control or feedback mechanism, and such that the charge density per phase applied to the nerve is below the predetermined threshold. As described elsewhere herein, the external trigger may be an external controller 101 operable by the operator to initiate application of a signal.

Microprocessor 113 of the implantable device 106, may be constructed so as to generate, in use, a preconfigured and/or operator-selectable signal that is independent of any input. In other embodiments, however, microprocessor 113 is responsive to an external signal, for example information (e.g. data) pertaining to one or more responses associated with sympatho-excitation of an effector.

Microprocessor 113 may be triggered upon receipt of a signal generated by an operator, such as a physician or the subject in which the implantable device 106 is implanted. To that end, the implantable device 106 may be part of a system which additionally comprises an external system 118 comprising a controller 101. An example of such a system is described below with reference to FIG. 9.

External system 118 of system 100 is external to system 116 and external to the subject, and comprises controller 101. Controller 101 may be used for controlling and/or externally powering system 116. To this end, controller 101 may comprise a powering unit 102 and/or a programming unit 103. The external system 118 may further comprise a power transmission antenna 104 and a data transmission antenna 105, as further described below.

The controller 101 and/or microprocessor 113 may be configured to apply any one or more of the above signals to the nerve periodically or continuously. Periodic application of a signal involves applying the signal in an (on-off)$_n$ pattern, where n≥1. For instance, the signal can be applied continuously for a duration of at least 5 days, optionally at least 7 days, before ceasing for a period (e.g. 1 day, 2 days, 3 days, 1 week, 2 weeks, 1 month), before being again applied continuously for another duration of at least 5 days, etc. Thus the signal is applied for a first time period, then stopped for a second time period, then reapplied for a third time period, then stopped for a fourth time period, etc. In such an embodiment, the first, second, third and fourth periods run sequentially and consecutively. The duration of the first, second, third and fourth time periods is independently selected. That is, the duration of each time period may be the same or different to any of the other time periods. In certain such embodiments, the duration of each of the first, second, third and fourth time periods may be any time from 1 second (s) to 10 days (d), 2 s to 7 d, 3 s to 4 d, 5 s to 24 hours (24 h), 30 s to 12 h, 1 min to 12 h, 5 min to 8 h, 5 min to 6 h, 10 min to 6 h, 10 min to 4 h, 30 min to 4 h, or 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 2 d, 3 d, 4 d, 5 d, 6 d, or 7 d.

In certain embodiments, the signal is applied by controller 101 and/or microprocessor for a specific amount of time per day. In certain such embodiments, the signal is applied for a duration of 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, or 23 h per day. In certain such embodiments, the signal is applied continuously for the specified amount of time. In certain alternative such embodiments, the signal may be applied discontinuously across the day, provided the total time of application amounts to the specified time.

Continuous application may continue indefinitely, e.g. permanently. Alternatively, the continuous application may be for a minimum period, for example the signal may be continuously applied for at least 5 days, or at least 7 days.

Whether the signal applied to the nerve is controlled by controller 101, or whether the signal is continuously applied directly by microprocessor 113, although the signal might be a series of pulses, the gaps between those pulses do not mean the signal is not continuously applied.

For preventive use, a subject at risk of developing cardiac dysfunction may be subjected to signal application for x min at regular intervals, wherein x=≤3 min, ≤5 min, ≤10 min, ≤20 min, ≤30 min, ≤40 min, ≤50 min, ≤60 min, ≤70 min, ≤80 min, ≤90 min, ≤120 min, or ≤240 min. The interval may be once every day, once every 2 days, once every 3 days etc. The interval may be more than once a day, e.g. twice a day, three times a day etc.

In certain embodiments, the signal is applied only when the subject is in a specific state e.g. only when the subject is awake, only when the subject is asleep, prior to and/or after the ingestion of food, prior to and/or after the subject undertakes exercise, etc.

The various embodiments for timing for modulation of neural activity in the nerve can all be achieved using controller 101 in a system of the invention.

The controller 101 and/or microprocessor 113 may include means for determining the charge density per phase supplied to the nerve in the time period before the neural activity of the nerve returns to baseline activity. The controller 101 and/or microprocessor 113 may additionally include means for estimating the charge density per phase supplied to the nerve by a set of signal parameters.

Other Components of the System Including the Implantable Device

In addition to the aforementioned neural interfacing element (e.g. electrode 109), neural interface 108, and microprocessor 113, the system 116 may comprise one or more of the following components: implantable transceiver 110; physiological sensor 111; power source 112; memory 114 (otherwise referred to as a non-transitory computer-readable storage device); and physiological data processing module 115. Additionally or alternatively, the physiological sensor 111; memory 114; and physiological data processing module 115 may be part of a sub-system external to the system 116. Optionally, the external sub-system may be capable of communicating with the system, for example wirelessly via the implantable transceiver 110.

In some embodiments, one or more of the following components may be contained in the implantable device 106: power source 112; memory 114; and a physiological data processing module 115.

The power source 112 may comprise a current source and/or a voltage source for providing the power for the signal generator 117. The power source 112 may also provide power for the other components of the implantable device 106 and/or system 116, such as the microprocessor 113, memory 114, and implantable transceiver 110. The power source 112 may comprise a battery, the battery may be rechargeable. The implantable device 106 and/or system 116 may be powered by inductive powering or a rechargeable power source.

It will be appreciated that the availability of power is limited in implantable devices, and the invention has been devised with this constraint in mind. The invention in particular modulates a nerve according to the invention with an electrical signal with a charge density per phase below a predetermined threshold, where the threshold is defined as the minimum charge density per phase reduce sympatho-excitation in the effector in the subject. This is different from conventional devices, such as that in reference [9] which aim to evoke a response associated with sympatho-excitation of an effector by modulating the nerve above the predetermined threshold, and hence require greater amounts of electrical charge than the invention for the treatment of one of the diseases discussed below (e.g. cardiac dysfunction). The low electrical charge required for treatment by the invention results in a lower amount of electrical energy being required for the treatment. This is advantageous as it reduces the burden on the implantable device and/or system for generating power, allowing the device and/or system to be smaller and lighter. Furthermore, in the case that the power source is not powered by inductive powering, the power source does not need to be changed as often. Changing a power source such as a battery in implanted devices such as the invention can be risky as it generally involves surgery. Methods for converting a charge density per phase into electrical energy for a given device are well known in the art.

Memory 114 may store power data and data pertaining to a response associated with sympatho-excitation of an effector, from system 116. For instance, memory 114 may store data pertaining to one or more physiological parameters (which are further discussed below) detected by physiological sensor 111, and/or the one or more corresponding a response associated with sympatho-excitation of an effector determined via physiological data processing module 115. In addition or alternatively, memory 114 may store power data and data pertaining to the physiological parameters and/or responses associated with sympatho-excitation of an effector from external system 118 via the implantable transceiver 110. For instance, memory 114 may store how much charge density per phase has been applied to the nerve, or how much charge density per phase the controller 101 and/or microprocessor 113 estimates will be applied to the nerve by a set of signal parameters. To this end, the implantable transceiver 110 may form part of a communication subsystem of the system 100, as is further discussed below.

Physiological data processing module 115 is configured to process one or more physiological parameters detected by the physiological sensor 111, to determine one or more corresponding a response associated with sympatho-excitation of an effector. Physiological data processing module 115 may be configured for reducing the size of the data pertaining to the one or more physiological parameters for storing in memory 114 and/or for transmitting to the external system via implantable transceiver 110. Implantable transceiver 110 may comprise one or more antenna(e). The implantable transceiver 100 may use any suitable signaling process such as RF, wireless, infrared and so on, for transmitting signals outside of the body, for instance to system 100 of which the system 116 is one part.

Alternatively or additionally, physiological data processing module 115 may be configured to process the one or more physiological parameters and/or process the determined responses in the subject to determine the evolution of a medical condition. In such case, the system 116, in particular the implantable device 106, will include a capability of calibrating and tuning the signal parameters based on the one or more physiological parameters of the subject and the determined evolution of the medical condition in the subject, as is further discussed below. In calibrating and tuning the signal parameters, the system 116 must ensure, via the controller 101 and/or microprocessor 113 that the charge density per phase applied to the nerve by the calibrated signal parameters is below the predetermined threshold. To this end, controller 101 and/or microprocessor 113 may store to memory the charge density per phase that has been applied, and the physiological sensor 111 may detect neural activity in the nerve to determine if the neural activity has returned to baseline activity. When the physiological sensor 111 detects neural activity has returned to baseline activity, the controller 101 and/or microprocessor 113 may reset the stored value of the charge density per phase applied.

The physiological data processing module 115 and the at least one physiological sensor 111 may form a physiological sensor subsystem, also known herein as a detector, either as part of the system 116, part of the implantable device 106, or external to the system 116.

Physiological sensor 111 comprises one or more sensors, each configured to detect one of the one or more physiological parameters described in detail below. For example, the physiological sensor 110 is configured for one or more of: detecting the heart rate using a heart rate monitor, detecting electrical activity of the heart and/or heart rhythm using an electrical sensor (e.g. an ECG recorder); detecting blood pressure (e.g. ventricular pressure) using a pressure sensor; or a combination thereof. Alternatively, the physiological sensor 111 comprises at least one recording electrodes positioned on one of the at least one neural interfaces, to detect neural activity in the sympathetic chain. Preferably, in embodiments where the nerve is a cardiac-related sympathetic nerve, as shown in FIG. 7B, the at least one neural interface is positioned on the branch between the T2-T3 ganglia.

The physiological parameters determined by the physiological data processing module 115 may be used to trigger the microprocessor 113 to apply a signal of the kinds described above to a nerve according to the invention using the neural interfacing element (e.g. electrode 109). Upon receipt of the physiological parameter received from physiological sensor 111, the physiological data processor 115 may determine the physiological parameter of the subject, and the evolution of the medical condition, by calculating in accordance with techniques known in the art.

The memory 114 may store physiological data pertaining to normal levels of the one or more physiological parameters. The data may be specific to the subject into which the system 116 is implanted, and gleaned from various tests known in the art. Upon receipt of the physiological parameter received from physiological sensor 111, or else periodically or upon demand from physiological sensor 111, the physiological data processor 115 may compare the physiological parameter determined by the signal received from physiological sensor 111 with the data pertaining to a normal level of the physiological parameter stored in the memory 114, and determine whether the received physiological parameter is indicative of the evolution of the medical condition in the subject.

The system 116 and/or implantable device 106 may be configured such that if and when an insufficient or excessive level of a physiological parameter is determined by physiological data processor 115, the physiological data processor 115 triggers apply of a signal to a nerve according to the invention by the neural interfacing element in the manner described elsewhere herein. For instance, if physiological parameter indicative of worsening of cardiac function, the physiological data processor 115 may trigger apply of a signal which dampens the worsening cardiac dysfunction, as described elsewhere herein. Particular physiological parameters relevant to the present invention are described above. When one or more of these physiological parameters are received by the physiological data processor 115, a signal may be applied to the nerve.

As an alternative to, or in addition to, the ability of the system 116 and/or implantable device 106 to respond to physiological parameters of the subject, the microprocessor 113 may be triggered upon receipt of a signal generated by an operator (e.g. a physician or the subject in which the system 116 is implanted). To that end, the system 116 may be part of a system 100 which comprises external system 118 and controller 101, as is further described below.

System Including Implantable Device

With reference to FIG. 9, the implantable device 106 of the invention may be part of a system 100 that includes a number of subsystems, for example the system 116 and the external system 118. The external system 118 may be used for powering, programming and providing operator interaction with the system 116 and/or the implantable device 106 through human skin and underlying tissues. The implantable device 106 applying a signal according to the present disclosure may be configured either externally or internally.

The external subsystem 118 may comprise, in addition to controller 101, one or more of: a powering unit 102, for wirelessly recharging the battery of power source 112 used to power the implantable device 106; a programming unit 103 configured to communicate with the implantable transceiver 110. The programming unit 103 and the implantable transceiver 110 may form a communication subsystem. In some embodiments, powering unit 102 is housed together with programing unit 103. In other embodiments, they can be housed in separate devices.

The external subsystem 118 may also comprise one or more of: power transmission antenna 104; and data transmission antenna 105. Power transmission antenna 104 may be configured for transmitting an electromagnetic field at a low frequency (e.g., from 30 kHz to 10 MHz). Data transmission antenna 105 may be configured to transmit data for programming or reprogramming the implantable device 106, and may be used in addition to the power transmission antenna 104 for transmitting an electromagnetic field at a high frequency (e.g., from 1 MHz to 10 GHz). The temperature in the skin will not increase by more than 2 degrees Celsius above the surrounding tissue during the operation of the power transmission antenna 104. The at least one antennae of the implantable transceiver 110 may be configured to receive power from the external electromagnetic field generated by power transmission antenna 104, which may be used to charge the rechargeable battery of power source 112.

The power transmission antenna 104, data transmission antenna 105, and the at least one antennae of implantable transceiver 110 have certain characteristics such a resonant frequency and a quality factor (Q). One implementation of the antenna(e) is a coil of wire with or without a ferrite core forming an inductor with a defined inductance. This inductor may be coupled with a resonating capacitor and a resistive loss to form the resonant circuit. The frequency is set to match that of the electromagnetic field generated by the power transmission antenna 105. A second antenna of the at least one antennae of implantable transceiver 110 can be used in system 116 for data reception and transmission from/to the external system 118. If more than one antenna is used in the system 116, these antennae are rotated 30 degrees from one another to achieve a better degree of power transfer efficiency during slight misalignment with the with power transmission antenna 104.

External system 118 may comprise one or more external body-worn physiological sensors 121 (not shown) to detect one or more physiological parameters. The signals may be transmitted to the system 116 via the at least one antennae of implantable transceiver 110. Alternatively or additionally, the signals may be transmitted to the external system 116 and then to the system 116 via the at least one antennae of implantable transceiver 110. As with physiological parameters detected by the implanted physiological sensor 111, the physiological parameters detected by the external sensor 121 may be processed by the physiological data processing module 115 to determine the one or more physiological parameters and/or stored in memory 114 to operate the system 116 in a closed-loop fashion. The physiological parameters of the subject determined via signals received from the external sensor 121 may be used in addition to alternatively to the physiological parameters determined via signals received from the implanted physiological sensor 111.

The system 100 may include a safety protection feature that discontinues the electrical modulation of a nerve according to the invention in the following exemplary events: abnormal operation of the system 116 (e.g. overvoltage); abnormal readout from an implanted physiological sensor 111 (e.g. temperature increase of more than 2 degrees Celsius or excessively high or low electrical impedance at the electrode-tissue interface); abnormal readout from an external body-worn physiological sensor 121 (not shown); abnormal response to modulation detected by an operator (e.g. a physician or the subject); or the charge density per phase applied to the nerve goes above the predetermined threshold. The safety precaution feature may be implemented via controller 101 and communicated to the system 116, or internally within the system 116.

The external system 118 may comprise an actuator 120 (not shown) which, upon being pressed by an operator (e.g. a physician or the subject), will apply a signal, via controller 101 and the respective communication subsystem, to trigger the microprocessor 113 of the system 116 to apply a signal to the nerve by the neural interfacing element (e.g. electrode 109).

System 100 of the invention, including the external system 118, but in particular system 116, is preferably made from, or coated with, a biostable and biocompatible material. This means that the system 116 is both protected from damage due to exposure to the body's tissues and also minimizes the risk that the system 116 produces an unfavorable reaction by the host (which could ultimately lead to rejection). The material used to make or coat the system 116 should ideally resist the formation of biofilms. Suitable materials include, but are not limited to, poly(p-xylylene) polymers (known as Parylenes) and polytetrafluoroethylene.

The implantable device 116 of the invention will generally weigh less than 50 g.

Application in Therapy

The invention involves treating and preventing conditions where the pathology is driven by exacerbated sympatho-excitation. For example, cardiac dysfunction, or metabolic disorders which involve impaired glucose control, such as T2D.

Treatment of the conditions described herein can be assessed in various ways, but typically involves determining an improvement in one or more responses of the subject. As used herein, an "improvement in a response" is taken to mean that, for any given response in a subject, an improvement is a change in a value indicative of that response (i.e. a change in a physiological parameter) in the subject towards the normal value or normal range for that value—i.e. towards the expected value in a healthy subject. That response is a response that is associated with the reduction in sympatho-excitation in the effector.

As used herein, worsening of the effector function is taken to mean that, for any given response in a subject, worsening is a change in a value indicative of that response in the subject away from the normal value or normal range for that value—i.e. away from the expected value in a healthy subject.

The invention may also involve detecting one or more physiological parameters of the subject, and hence responses associated with sympatho-excitation in the effector, which is indicative of effector function. This may be done before, during and/or after modulation of neural activity in the sympathetic nerve according to the invention. The physiological parameter may be organ-based or neuro-based, as described further below.

For preventive use, a subject at risk of developing a condition where the pathology is driven by exacerbated sympatho-excitation may be subjected to signal application for x min at regular intervals, wherein x=≤3 min, ≤5 min, ≤10 min, ≤20 min, ≤30 min, ≤40 min, ≤50 min, ≤60 min, ≤70 min, ≤80 min, ≤90 min, ≤120 min, or ≤240 min. The interval may be once every day, once every 2 days, once every 3 days etc. The interval may be more than once a day, e.g. twice a day, three times a day etc.

A subject suitable for the invention may be any age, but will usually be at least 40, 45, 50, 55, 60, 65, 70, 75, 80 or 85 years of age.

As used herein, a physiological parameter is not affected by modulation of the neural activity of the sympathetic nerve according to the invention if the parameter does not change (in response to the sympathetic nerve activity modulation) from the normal value or normal range for that value of that parameter exhibited by the subject or subject when no intervention has been performed i.e. it does not depart from the baseline value for that parameter.

The skilled person will appreciate that the baseline for any neural activity or physiological parameter in an subject need not be a fixed or specific value, but rather can fluctuate within a normal range or may be an average value with associated error and confidence intervals. Suitable methods for determining baseline values are well known to the skilled person.

As used herein, a physiological parameter is determined in a subject when the value for that parameter exhibited by the subject at the time of detection is determined. A detector (e.g. a physiological sensor subsystem, a physiological data processing module, a physiological sensor, etc.) is any element able to make such a determination.

Thus, in certain embodiments, the invention further comprises a step of determining one or more physiological parameters of the subject, wherein the signal is applied only when the determined physiological parameter meets or exceeds a predetermined threshold value. In such embodiments wherein more than one physiological parameter of the subject is determined, the signal may be applied when any one of the determined physiological parameters meets or exceeds its threshold value, alternatively only when all of the determined physiological parameters meet or exceed their threshold values. In certain embodiments wherein the signal is applied by a system of the invention, the system further comprises at least one detector configured to determine the one or more physiological parameters of the subject.

In certain embodiments, the physiological parameter is an action potential or pattern of action potentials in a nerve of the subject, wherein the action potential or pattern of action potentials is associated with the condition that is to be treated. For example, the nerve is the sympathetic nerve according to the invention. In this embodiment, the pattern of action potentials determined by the at least one detector may be associated with a condition where the pathology is driven by exacerbated sympatho-excitation, e.g. cardiac dysfunction.

It will be appreciated that any two physiological parameters may be determined in parallel embodiments, the controller is coupled detect the pattern of action potentials tolerance in the subject.

A predetermined threshold value for a physiological parameter is the minimum (or maximum) value for that parameter that must be exhibited by a subject or subject before the specified intervention is applied. For any given parameter, the threshold value may be defined as a value indicative of a pathological state or a disease state, or as a value indicative of the onset of a pathological state or a disease state. Thus, depending on the predetermined threshold value, the invention can be used as a treatment. Alternatively, the threshold value may be defined as a value indicative of a physiological state of the subject (that the subject is, for example, asleep, post-prandial, or exercising). Appropriate values for any given physiological parameter would be simply determined by the skilled person (for example, with reference to medical standards of practice).

Such a threshold value for a given physiological parameter is exceeded if the value exhibited by the subject is beyond the threshold value—that is, the exhibited value is a greater departure from the normal or healthy value for that physiological parameter than the predetermined threshold value.

Treatment and Prevention of Cardiac Dysfunction

The invention involves treating or preventing cardiac dysfunction.

Increased sympathetic tone is associated with various cardiac conditions, e.g. heart failure, myocardial infarction, hypertension and cardiac arrhythmias. Hence in the embodiments where the effector is the heart, the invention is particularly useful for treating or preventing these conditions.

In the embodiments where the effector is the foregut, the invention may lead to lowering of mesenteric vascular resistance, and so in such embodiments the invention is particularly useful for treating hypertension or heart failure.

The conditions associated with cardiac dysfunction are described further below.

Heart failure is a condition caused by the heart failing to pump enough blood around the body to meet the demands of peripheral tissues. Heart failure may present itself as congestive heart failure (CHF) due to the accompanying venous and pulmonary congestion. Heart failure can be due to a variety of etiologies such as ischemic heart disease. Cardiac decompensation is typically marked by dyspnea (difficulty breathing), venous engorgement and edema, and each decompensation event can cause further long term deterioration of the heart function. Heart failure patients have reduced autonomic balance, typically with a sympathetic overdrive, which is associated with left ventricular dysfunction and increased mortality. Heart failure, such as HFREF (heart failure with reduced ejection fraction) and HFpEF (heart failure with preserved ejection faction), are particularly useful with the invention.

Myocardial infarction occurs when myocardial ischemia, a diminished blood supply to the heart, exceeds a critical threshold and results in irreversible myocardial cell damage or death.

The invention is also useful in treating or preventing hypertension. A subject who has hypertension has a blood pressure of 140/90 mmHg or higher. In a normal subject, the ideal blood pressure is considered to be between 90/60 mmHg and 120/80 mmHg. The invention may relate to treating or preventing cardiac arrhythmia, also called cardiac dysrhythmia (or simply irregular heart beat), which refers to a group of conditions in which there is abnormal electrical activity in the heart. Some arrhythmias are life-threatening medical emergencies that can result in cardiac arrest and sudden death. Other cause symptoms such as an abnormal awareness of heart beat. Others may not be associated with any symptoms at all but predispose toward potentially life-threatening stroke, embolus or cardiac arrest. Cardiac arrhythmia can be classified by rate (physiological, tachycardia or bradycardia), mechanism (automaticity, re-entry or fibrillation) or by site of origin (ventricular or supraventricular).

Preferably, the invention relates to treating or preventing ventricular arrhythmia, e.g. ventricular tachycardia (VT) and ventricular fibrillation (VF). Ventricular arrhythmias are characterized by a disruption in the normal excitation-contraction rhythm of heart. In particular, VT and VF are characterized by abnormally rapid, asynchronous contraction of the ventricles. As such, the heart is unable to adequately pump oxygenated blood to the systemic circulation. If not treated immediately, ventricular arrhythmias can lead to additional tissue damage or patient death. These potentially life threatening events are characterized by, among other things, an increase in transient calcium currents and an elevation in diastolic calcium concentration in cardiac tissue, lengthening of the cardiac action potential, a drop in blood pressure and ischemia (lack of adequate blood flow to the heart). These changes can potentially affect the return of spontaneous circulation, hemodynamics, refibrillation and resuscitation success.

The invention is useful for subjects who are at risk of developing cardiac dysfunction. These subjects may be subjected to application of the signals described herein, thereby decreasing the arrhythmic burden. The cardiac testing strategies for subjects at risk of cardiac dysfunction are known in the art, e.g. heart rate variability (HRV), baroreflex sensitivity (BRS), heart rate turbulence (HRT), heart rate deceleration capacity (HRDC) and T wave alternans (TWA). Deviation of these parameters from the baseline value range would be an indication of the subject being at risk of developing cardiac dysfunction.

Other indications include when the subject has a history of cardiac problems or a history of myocardium injury. For example, the subject has undergone heart procedures, e.g. heart surgery. The subject may have had a myocardial infarction. The subject may have emphysema or chronic obstructive pulmonary disease. The subject may have a history of arrhythmia or is genetically pre-disposed to arrhythmia.

The invention can be used in combination with conventional anti-arrhythmia therapies. For example, some arrhythmias, e.g. atrial fibrillation, cause blood clotting within the heart and increase risk of embolus and stroke. Anticoagulant medications such as warfarin and heparin, and anti-platelet drugs such as aspirin can reduce the risk of clotting. Thus, the invention can be used in combination with administering an anticoagulant. The invention also provides an anticoagulant medicine for use in treating a subject, wherein the subject has an implanted system of the invention in signaling contact with a cardiac-related sympathetic nerve in the extracardiac intrathoracic neural circuit.

An organ-based biomarker useful for the invention may be any measurable physiological parameter of the heart. For example, a physiological parameter may be one or more of the group consisting of: heart rate, heart rhythm, conduction and heart contractility (e.g. ventricular pressure, ventricular contractility, activation-recovery interval, effective refractory period, stroke volume, ejection fraction, end diastolic fraction, stroke work, and arterial elastance). These parameters may indicate a chronotropic response, a dromotropic response, a lusitropic response and/or an inotropic response.

Chronotropic responses refer to changes in the heart rate and/or rhythm. These effects may be indicated using known techniques in the art, such as by electrocardiography, e.g. using the RR-interval.

Dromotropic responses refer to changes to the conduction speed in the atrioventricular (AV) node. These effects may be indicated using known techniques in the art, such as by electrocardiography, e.g. using the PR-interval which would indicate the electrical spread across the atria to the AV-node.

Lusitropic responses refer to the changes in the rate of myocardial relaxation. These effects may be indicated using known techniques in the art, such as by measuring the rate of pressure change in the ventricle (e.g. dP/dT).

Inotropic responses refer to the strength of contraction of heart muscle (i.e. myocardial contractility). These effects may be indicated using known techniques in the art, such as by measuring the rate of pressure change in the ventricle (e.g. dP/dT).

Respiration parameters may also be useful. They can be derived from, for example, a minute ventilation signal and a fluid index can be derived from transthoracic impedance. For example decreasing thoracic impedance reflects increased fluid buildup in lungs, and indicates a progression of heart failure. Respiration can significantly vary minute ventilation. The transthoracic impedance can be totaled or averaged to provide an indication of fluid buildup.

Heart Rate Variability (HRV) a technique useful for assess autonomic balance. HRV relates to the regulation of the sinoatrial node, the natural pacemaker of the heart by the sympathetic and parasympathetic branches of the autonomic nervous system. An HRV assessment is based on the assumption that the beat-to-beat fluctuations in the rhythm of the heart provide us with an indirect measure of heart health, as defined by the degree of balance in sympathetic and parasympathetic nerve activity.

The invention may involve assessing the heart rate by methods known in the art, for example, with a stethoscope or by feeling peripheral pulses. These methods cannot usually diagnose specific arrhythmias but can give a general indication of the heart rate and whether it is regular or irregular. Not all of the electrical impulses of the heart produce audible or palpable beats; in many cardiac arrhythmias, the premature or abnormal beats do not produce an effective pumping action and are experienced as "skipped" beats.

The invention may also involve assessing the heart rhythm. For example, the simplest specific diagnostic test for assessment of heart rhythm is the electrocardiogram (abbreviated ECG or EKG). A Holter monitor is an EKG recorded over a 24-hour period, to detect arrhythmias that can happen briefly and unpredictably throughout the day.

Other useful assessment techniques include using a cardiac event recorder; performing an electrophysiological (EP) study or performing an echocardiogram.

The invention may involve assessing a neuro-based biomarker. Hence, in some embodiments, the physiological parameter may be one or more abnormal cardiac electrical signals from the subject indicative of cardiac dysfunction. The abnormal cardiac electrical signals may be measured in a cardiac-related intrathoracic nerve or peripheral ganglia of the cardiac nervous system. The abnormal electric signals may be a measurement of cardiac electric activity.

Example of assessing cardiac electrical signals include microneurography or plasma noradrenaline concentration. Miconeurography involves using fine electrodes to record 'bursts' of activity from multiple or single afferent and efferent nerve axons [26,27]. The measurement of regional plasma noradrenaline spillover is useful in providing information on sympathetic activity in individual organs. Following nerve depolarization, any remaining noradrenaline in the synapse, the 'spillover', is washed out into the plasma and the plasma concentration is therefore directly related to the rate of sympathetic neuronal discharge [28,29,30].

For an example, in a subject having cardiac dysfunction, an improvement, and hence indicating a reduction in sympatho-excitation in the effector, may be indicated by a decrease in a chronotropic evoked response, a decrease in a dromotropic evoked response, a decrease in a lusitropic evoked response and/or a decrease in an inotropic evoked response. An improvement in a measurable physiological parameters, and hence indicating a reduction in sympatho-excitation in the effector, may be a decrease in heart rate, conduction or heart contractility (e.g. ventricular pressure, ventricular contractility, activation-recovery interval, effective refractory period, stroke volume, ejection fraction, end diastolic fraction, stroke work, arterial elastance). The invention might not lead to a change in all of these parameters. Suitable methods for determining the value for any given parameter will be appreciated by the skilled person.

In certain embodiments of the invention, treatment of the condition is indicated by an improvement in the profile of neural activity in the cardiac-related sympathetic nerve. That is, treatment of the condition is indicated by the neural activity in the cardiac-related sympathetic nerve approaching the neural activity in a healthy subject.

Treatment of Conditions Associated with Impaired Glucose Control

In embodiments where the effector is the foregut, the invention involves treating subjects suffering from conditions associated with impaired glucose control. Conditions associated with impaired glucose control include those conditions thought to cause the impairment (for example insulin resistance, obesity, metabolic syndrome, Type 1 diabetes, Hepatitis C infection, acromegaly) and conditions resulting from the impairment (for example obesity, sleep apnoea syndrome, dyslipidaemia, hypertension, Type 2 diabetes). It will be appreciated that some conditions can be both a cause of and caused by impaired glucose control. Other conditions associated with impaired with glucose control would be appreciated by the skilled person. It will also be appreciated that these conditions may also be associated with insulin resistance.

The invention is of particular interest in relation to insulin resistance, prediabetes, and type 2 diabetes.

As used herein, "impaired glucose control" is taken to mean an inability to maintain blood glucose levels at a normal level (i.e. within normal limits for a healthy individual). As will be appreciated by the skilled person, this will vary based on the type of subject and can be determined by a number of methods well known in the art, for example a glucose tolerance test (GTT). For example, in humans undergoing an oral glucose tolerance test, a glucose level at 2 hours of less than or equal to 7.8 mmol/L is considered normal. A glucose level at 2 hours of more than 7.8 mmol/L is indicative of impaired glucose control.

As used herein, "insulin resistance" has its normal meaning in the art i.e. in subject or patient exhibiting insulin resistance, the physiological response to insulin in the subject or patient is refractory, such that a higher level of insulin is required in order to control blood glucose levels, compared to the insulin level required in a healthy individual. Insulin sensitivity is used herein as the reciprocal to insulin resistance—that is, an increase in insulin sensitivity equates to a decrease in insulin resistance, and vice versa. Insulin resistance may be determined using any method known in the art, for example a GTT, a hyperinsulinaemic clamp or an insulin suppression test.

Treatment of the condition associated with impaired glucose control can be assessed in various ways, but typically involves an improvement in one or more detected physiological parameters, and hence assessing responses that are associated with the reduction in sympatho-excitation in the effector. For an example, in a subject having a condition associated with impaired glucose control (e.g. insulin resistance) an improvement in a measurable parameter (and hence a response associated with the reduction in sympatho-excitation in the effector) may (depending on which abnormal values a subject is exhibiting) be one or more of: an increase in insulin sensitivity, a decrease in insulin resistance, a decrease in (fasting) plasma glucose concentration, a reduction in total fat mass, a reduction in visceral fat mass, a reduction in subcutaneous fat mass, a reduction in body mass index, a reduction in obesity, a reduction in sympathetic tone, blood pressure, a reduction in plasma and/or tissue catecholamines, reduction in urinary metanephrines, a reduction in glycated haemoglobin (HbA1c), and/or a reduction in circulating triglycerides. The invention might not lead to a change in all of these parameters.

In such embodiments, sympathetic tone is understood to be the neural activity in sympathetic nerves and/or associated sympathetic neurotransmitter measured in systemic or local tissue compartments in the sympathetic nervous system. Suitable methods for determining the value for any given parameter will be appreciated by the skilled person. By way of example, an increase in heart rate and/or blood pressure for a period at least 24 hrs is typically indicative of an increased sympathetic tone, as is aberrant heart rate variability, cardiac or renal norepinephrine spillover, skin or muscle microneurography and plasma/urine norepinephrine. By way of further example, insulin sensitivity can be measured by the HOMA index or by a hyperinsulinemic clamp. By way of further example, total fat mass may be determined by bioimpedence. By way of further example, visceral fat can be indirectly determined by measuring abdominal perimeter. Further suitable methods for determining the value for any given parameter would be appreciated by the skilled person.

In certain embodiments of the invention, treatment of the condition is indicated by an improvement in the profile of neural activity in the GSN. That is, treatment of the condition is indicated by the neural activity in the GSN approaching the neural activity in a healthy individual.

Ideally, a subject displays an improvement in glucose tolerance as assessed by oral glucose tolerance test. Methods of the invention may be used to treat insulin resistance and T2D. The invention may also be used to treat metabolic syndrome.

As used herein, a physiological parameter is not affected by inhibition of GSN neural activity if the parameter does not change (in response to GSN activity inhibition) from the average value of that parameter exhibited by the subject or subject when no intervention has been performed i.e. it does not depart from the baseline value for that parameter.

In certain embodiments of the method, the one or more detected physiological parameters useful with the invention are one or more of the group consisting of: sympathetic tone, blood pressure, plasma insulin concentration, insulin sensitivity, plasma glucose concentration, glucose tolerance, total fat mass, visceral fat mass, plasma catecholamines (i.e. one or more of epinephrine, norepinephrine, metanephrine, normetanephrine and dopamine) content, tissue catecholamines content urinary metanephrines content, plasma HbA1c content and a reduction in circulating triglyceride concentration.

By way of example, a typical HbA1c content in a healthy human subject would be between 20-42 mmol/mol (4-6% of total Hb). An HbA1c content exceeding 42 mmol/mol may be indicative of a diabetic state.

In certain embodiments, the detected physiological parameter is an action potential or pattern of action potentials in a nerve of the subject, wherein the action potential or pattern of action potentials is associated with the condition associated with an impaired response to glucose that is to be treated. In certain such embodiments, the nerve is a sympathetic nerve.

In certain embodiments, the invention does not affect the cardiopulmonary regulation function of the GSN. In particular embodiments, the method does not affect one or more physiological parameters in the subject selected from the group consisting of: $pO_2$, $pCO_2$, blood pressure, oxygen demand and cardio-respiratory responses to exercise and altitude. Suitable methods for determining the value for any given parameter would be appreciated by the skilled person.

A subject of the invention may, in addition to having an implant, receive medicine for their condition. For instance, a subject having an implant according to the invention may receive a diabetes medicine (which will usually continue medication which was occurring before receiving the implant). Such medicines include, but are not limited to: metformin; sulfonylureas, such as glyburide, glipizide, or glimepiride; meglitinides, such as repaglinide or nateglinide; thiazolidinediones, such as rosiglitazone or pioglitazone; DPP-4 inhibitors, such as sitagliptin, vildagliptin, saxagliptin or linagliptin; GLP-1 receptor agonists, such as exenatide or liraglutide; SGLT2 inhibitors, such as canagliflozin or dapagliflozin. Thus the invention provides the use of these medicines in combination with a device/system of the invention.

General

The term "electrode" refers to a unipolar electrode unless otherwise specified.

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" and "around" in relation to a numerical value x is optional and means, for example, x±10%.

Unless otherwise indicated each embodiment as described herein may be combined with another embodiment as described herein.

REFERENCES

[1] Vaseghi et al., Heart Rhythm, 2014; 11:360-366.
[2] Schwartz, Nat. Rev. Cardiol., 2014; 11, 346-353.

[3] Coleman et al., 2012: Circ Arrhythm Electrophysiol; 5(4):782-8.
[4] Hofferberth et al., 2014: J Thorac Cardiovasc Surg; 147(1):404-9.
[5] U.S. Pat. No. 7,734,355.
[6] U.S. Pat. No. 6,885,888.
[7] PCT/EP2017/071475.
[8] Janse et al., 1985, Circulation, 72(3):585-595.
[9] Ben-David et al., 1988; Circulation, 78:1241-1250.
[10] Ahmed and Wieraszko, 2009; 3, 1-12.
[11] U.S. provisional application 62/454,550.
[12] Groat and Saum, J. Physiol. 1972; 220, 297-314.
[13] Ardell et al., J. Physiol. 2017; doi:10.1113/JP274678
[14] Armour et al., Anatomy of the extrinsic autonomic nerves and ganglia innervating the mammalian heart. In: Randall W C, ed. Nervous control of cardiovascular function. New York: Oxford University Press; 1984; 21-67.
[15] Janes et al., Am J Cardiol.; 1986; 57:299-309.
[16] Buckley et al., Hear Rhythm 2016; 13(1): 282-288.
[17] Ajijola et al., Circ Arrhythm Electrophysiol. 2012; 5: 1010-1116.
[18] Han et al., J Am Coll Cardiol. 2012, 59:954-961.
[19] Loukas et al. (2010) *Clinical Anatomy* 23:512-22.
[20] Chen et al., 2010; Neurogastroenterol Motil., 22(10): 1109-e286.
[21] PCT/EP2017/062193.
[22] Lee et al., 2016; *Toxins* (*Basel*) 8(2): 51.
[23] Ye et al., 2012; J. Neuroscience, 32(25):8560-85683
[24] Sweeney, J. D., and J. T. Mortimer, 1986; IEEE Trans Biomed Eng 33: 541-9.
[25] Ungar et al. 1986; Ann Biomed Eng 14: 437-50.
[26] Vallbo et al. Physiological Reviews 1979; 59, 919-957.
[27] Macefield et al. The Journal of Physiology (London) 1994; 481, 799-809.
[28] Esler et al. Hypertension, 1988; 11, 3-20.
[29] Brown, G. L. & Gillespie, J. S. Journal of Physiology 1975; 138, 81-102.
[30] Grassi, G. & Esler, M. Journal of Hypertension, 1999; 17, 719-734.

The invention claimed is:

1. A system for reversibly modulating neural activity of a sympathetic nerve for treating impaired glucose control, wherein the system comprises:
at least two neural interfacing elements suitable for placement on or around the sympathetic nerve adjacent to a ganglion, wherein the ganglion transmits sympathetic signals between the ganglion and an effector; and
at least one voltage or current source configured to generate at least one electrical signal with a charge density per phase to be applied to the sympathetic nerve, via the at least two neural interfacing elements, to modulate the neural activity of the sympathetic nerve,
wherein the at least two neural interfacing elements are arranged such that the electrical signal incites action potentials in the sympathetic nerve that preferentially propagate either away from the effector towards the ganglion or towards the effector and away from the ganglion, wherein a first neural interfacing element is positioned along a nerve axis adjacent to a second neural interfacing element, and arranged such that the second neural interfacing element is closer to the effector along the nerve axis than the first neural interfacing element,
wherein the charge density per phase applied to the sympathetic nerve by the electrical signal is below a predetermined threshold,
the predetermined threshold defined as a minimum charge density per phase required to produce a response associated with sympatho-excitation in the effector by modulating the neural activity of the sympathetic nerve in order to treat impaired glucose control.

2. The system of claim 1, wherein the at least two neural interfacing elements comprises at least a first electrode and a second electrode.

3. The system of claim 2, wherein the first electrode is configured to be a cathode and the second electrode is configured to be an anode.

4. The system of claim 2, wherein the first electrode is configured to be an anode and the second electrode is configured to be a cathode.

5. The system of claim 2, wherein the first electrode and second electrode have an unbalanced current density.

6. The system of claim 2, wherein the first electrode and second electrode have an imbalanced surface area configuration.

7. The system of claim 2, wherein the first electrode and second electrode have an imbalanced insulation configuration.

8. The system of claim 1, wherein the at least one electrical signal to be applied to the sympathetic nerve has a pulse train waveform.

9. The system of claim 8, wherein the pulse train waveforms have a pulse duration of ≤2 ms.

10. The system of claim 1, wherein the at least one electrical signal has a frequency of ≤10 Hz.

11. The system of claim 1, wherein the charge density per phase applied to the sympathetic nerve by the electrical signal is between $0.1\tau$ and $0.9\tau$, where $\tau$ is the predetermined threshold.

12. The system of claim 1, wherein the predetermined threshold is ≤80 µC/cm²/phase.

13. The system of claim 1, wherein the ganglion is a suprarenal ganglion, and at least two neural interfacing elements suitable are configured to be placed on the sympathetic nerve between the suprarenal ganglion and a celiac ganglion.

14. The system of claim 1, wherein the ganglion is the celiac ganglia, and the first and second electrodes are configured to be placed on the sympathetic nerve between the celiac ganglion and the foregut.

15. A method of reversibly modulating neural activity in a sympathetic nerve, comprising:
(i) implanting in a subject a system of claim 1;
(ii) positioning the at least two neural interfacing elements of the system at the sympathetic nerve adjacent to a ganglion; and optionally
(iii) activating the system.

16. The method of claim 15, wherein the method is for treating or preventing impaired glucose control, wherein the effector is an organ in a foregut, further comprising assessing a change in a response associated with sympatho-excitation of the organ in the foregut, the response comprising an increase in blood pressure, an increase in heart rate or an increase in myocardial contractility.

17. A method for reversibly modulating neural activity of a sympathetic nerve in order to treat impaired glucose control, comprising:
placing at least two neural interfacing elements on or around the sympathetic nerve adjacent to a ganglion, wherein the ganglion transmits sympathetic signals between the ganglion and an effector; and applying, by at least one voltage or current source, at least one electrical signal with a charge density per phase to the sympathetic nerve, via the at least two neural interfacing elements to modulate the neural activity of the sympathetic nerve, wherein the at least two neural interfacing elements are arranged such that the electrical signal incites action potentials in the sympathetic nerve that preferentially propagate either away from the effector towards the ganglion or towards the effector and away from the ganglion, wherein the charge density per phase applied to the sympathetic nerve by the electrical signal is below a predetermined threshold, the predetermined threshold defined as a minimum charge density per phase required to produce a response associated with sympatho-excitation in the effector by modulating the neural activity of the sympathetic nerve in order to treat impaired glucose control.

18. The method of claim 17, wherein the effector is a foregut.

* * * * *